US009820987B2

(12) United States Patent
Lavitrano et al.

(10) Patent No.: US 9,820,987 B2
(45) Date of Patent: Nov. 21, 2017

(54) MODULATOR COMPOUNDS OF DRUG RESISTANCE IN EPITHELIAL TUMOR CELLS

(71) Applicant: BIONSIL S.R.L. in Liquidazione, Milan (IT)

(72) Inventors: Marialuisa Lavitrano, Milan (IT); Emanuela Grassilli, Monza (IT); Kristian Helin, Charlottelund (DK)

(73) Assignee: Bionsil S.R.L. in Liquidazione, Milan (IT)

( * ) Notice: Subject to any disclaimer, the term of this patent is extended or adjusted under 35 U.S.C. 154(b) by 0 days.

(21) Appl. No.: 14/586,051

(22) Filed: Dec. 30, 2014

(65) Prior Publication Data

US 2015/0111953 A1 Apr. 23, 2015

Related U.S. Application Data

(60) Continuation-in-part of application No. 14/514,147, filed on Oct. 14, 2014, now abandoned, which is a division of application No. 13/532,680, filed on Jun. 25, 2012, now Pat. No. 8,889,643, which is a division of application No. 12/531,061, filed as application No. PCT/EP2008/053099 on Mar. 14, 2008, now Pat. No. 8,232,085.

(30) Foreign Application Priority Data

Mar. 14, 2007 (IT) .............................. pd2007a000088
Apr. 13, 2007 (EP) ...................................... 07106119

(51) Int. Cl.
| | | |
|---|---|---|
| *A61K 48/00* | (2006.01) | |
| *C07H 21/02* | (2006.01) | |
| *C07H 21/04* | (2006.01) | |
| *A61K 31/519* | (2006.01) | |
| *A61K 31/513* | (2006.01) | |
| *A61K 45/06* | (2006.01) | |
| *A61K 31/277* | (2006.01) | |
| *A61K 31/505* | (2006.01) | |
| *A61K 31/506* | (2006.01) | |
| *A61K 31/713* | (2006.01) | |

(52) U.S. Cl.
CPC .......... *A61K 31/519* (2013.01); *A61K 31/277* (2013.01); *A61K 31/505* (2013.01); *A61K 31/506* (2013.01); *A61K 31/513* (2013.01); *A61K 31/713* (2013.01); *A61K 45/06* (2013.01)

(58) Field of Classification Search
CPC ............................ A61K 48/00; C12N 2310/11
See application file for complete search history.

(56) References Cited

U.S. PATENT DOCUMENTS

| | | | |
|---|---|---|---|
| 3,166,008 A | 1/1965 | Lewandoski | |
| 4,116,594 A | 9/1978 | Leanna et al. | |
| 5,815,994 A | 10/1998 | Hill et al. | |
| 5,856,094 A | 1/1999 | Sidransky et al. | |
| 5,989,885 A | 11/1999 | Teng et al. | |
| 6,303,652 B1 | 10/2001 | Uckun et al. | |
| 6,548,272 B1 | 4/2003 | Shimizu et al. | |
| 8,232,085 B2 * | 7/2012 | Lavitrano ............. | C12N 15/111 435/183 |
| 8,889,643 B2 * | 11/2014 | Lavitrano ............. | C12N 15/111 435/320.1 |
| 2001/0035104 A1 | 11/2001 | Gottling et al. | |
| 2002/0086838 A1 | 7/2002 | Oh et al. | |
| 2002/0178459 A1 | 11/2002 | McNeish et al. | |
| 2003/0037689 A1 | 2/2003 | Dreher et al. | |
| 2005/0051044 A1 | 3/2005 | Damm et al. | |
| 2005/0107386 A1 | 5/2005 | Narla et al. | |
| 2005/0246794 A1 | 11/2005 | Khvorova et al. | |
| 2005/0266561 A1 | 12/2005 | Wells | |
| 2007/0244312 A1 | 10/2007 | Khvorova et al. | |
| 2007/0275465 A1 | 11/2007 | Woppmann et al. | |
| 2008/0014583 A1 | 1/2008 | Montminy et al. | |
| 2008/0108583 A1 | 5/2008 | Feinstein | |
| 2009/0221679 A1 | 9/2009 | Espeseth et al. | |

FOREIGN PATENT DOCUMENTS

| | | |
|---|---|---|
| DE | 202005017869 | 7/2006 |
| EP | 1662259 A | 5/2006 |
| WO | 2002038797 | 5/2002 |
| WO | 2005056766 | 6/2005 |
| WO | 2006041902 | 4/2006 |
| WO | 2006063164 | 6/2006 |
| WO | 2006081418 | 8/2006 |
| WO | 2006113679 | 10/2006 |

OTHER PUBLICATIONS

Eschrich et al., "Molecular Staging for Survival Prediction of Colorectal Cancer Patients," J Clin Oncol 23 (15):3526-35 (2005).
Net Affymetrix (https://www.affymetrix.com/analysis/netaffx/showresults.affx, downloaded Dec. 19, 2014).
Machine Translation of DE202005017869 to David Wolf published Aug. 17, 2006.

(Continued)

*Primary Examiner* — Amy Bowman
(74) *Attorney, Agent, or Firm* — LeClairRyan, a Professional Corporation

(57) ABSTRACT

The described invention provides a method of treating a patient with an epithelial cancer comprising administering a composition comprising a therapeutic amount of an inhibitor of a BTK protein and one or more chemotherapeutic agent(s) selected from the group consisting of an antimetabolite, a platinum coordination compound, an alkylating agent and a combination thereof, wherein the composition is effective to reduce one or more of tumor cell growth, tumor cell clonogenicity, tumor cell proliferation, tumor cell viability and tumor volume and the therapeutic amount of the inhibitor of a BTK protein and the one or more chemotherapeutic agent(s) exerts a synergistic effect. The described invention also provides methods of treating a chemotherapy drug-resistant cancer and sensitizing a cancer patient to chemotherapy.

7 Claims, 25 Drawing Sheets

(56) References Cited

OTHER PUBLICATIONS

Hafner et al., "Differential Gene Expression of Eph Receptors and Ephrins in Benign Human Tissues and Cancers," Clin Chem 50(3):490-9 (2004).
Uckun et al., "Anti-breast Cancer Activity of LFM-A13, a Potent Inhibitor of Polo-like Kinase (PLK)," Bioorganic & Medicinal Chemistry 15(3):800-814 (2006).
Surawasa et al., "The Role of Ephrins and Eph Receptors in Cancer," Cytokine and Growth Factor Reviews 15(6):419-433 (2004).
Shakoori et al., "Dergulated GSK3beta Activity in Colorectal Cancer: Its Association with Tumor Cell Survival and Proliferation," Biochemical and Biophysical Research Communications 334(4):1365-1373 (2005).
Mayes et al., "Overcoming Drug Resistance of Hypoxic Cancer Cells and Tumors Via Stabilization of c-Myc Protein Through Inhibition of GSK3 Beta," Proceedings of the Annual Meeting of the American Association for Cancer Research, New York, NY, vol. 49th, p. 641, Apr. 1, 2008.
Mao et al., "EphB2 as a Therapeutic Antibody Drug Target for the Treatment of Colorectal Cancer," Cancer Research 64(3):781-8 (2004).
Hafner et al., "Expression Profile of Eph Receptors and Ephrin Ligands in Human Skin and Downregulation of Epha 1 in Nonmelanoma Skin Cancer," Modern Pathology 19(10):1369-77 (2006).
Masuda et al., "Fibronectin Type I Repeat is a Nonactivating Ligand for EphA1 and Inhibits ATF3-dependent Angiogenesis," J Biol Chem. 283(19):13148-55 (2008).
Levin et al., "Liposomal Delivery of EphA2 siRNA in Combination with Gemcitabine Reduces Pancreatic Tumor Growth and Invasion," Pancreas 33(4):477 (2006).
Landen et al., "Therapeutic EphA2 Gene Targeting in vivo Using Neutral Liposomal Small Interfering RNA Delivery," Cancer Research 65(15):6910-8 (2005).
De Toni et al., "A Crosstalk Between the Wnt and the Adhesion-dependent Signaling Pathways Governs the Chemosensitivity of Acute Myeloid Leukemia," Oncogene 25(22):3113-22 (2006).
Tan et al., "Pharmacologic Modulation of Glycogen Synthase Kinase-3beta Promotes p53-dependent Apoptosis Through a Direct Bax-mediated Mitochondrial Pathway in Colorectal Cancer Cells," Cancer Res. 65(19):9012-20 (2005).
Uckun et al., "In vivo Pharmacokinetic Features, Toxicity Profile, and Chemosensitizing Activity of Alpha-cyano-beta-hydroxy-beta-methyl-N-(2,5-dibromophenyl)propenamide (LFM-A13), a Novel Antileukemic Agent Targeting Bruton's Tyrosine Kinase," Clin Cancer Res. 8(5):1224-33 (2002).
"Colorectal Cancer" The Merck Manual, (online), Dec. 2007, pp. 1-5.
"Modalities of Cancer Therapy," The Merck Manual, (online), Nov. 2005, pp. 1-6.
Bartz et al., "Small Interfering RNA Screens Reveal Enhanced Cisplatin Cytotoxicity in Tumor Cells Having Both BRCA Network and TP53 Disruptions," Mol Cell Biol. 26(24):9377-86 (2006).
Chica et al., "Semi-rational Approaches to Engineering Enzyme Activity: Combining the Benefits of Directed Evolution and Rational Design," Curr. Opin. Biotechnol. 16(4):378-84 (2005).
Sen et al., "Developments in Directed Evolution for Improving Enzyme Functions," Appl. Biochem. Biotechnol. 143 (3):212-23 (2007).
Accession No. Q06187, published Jun. 1, 1994.
Accession No. P35991, published Jun. 1, 2994.
Afar et al., "Regulation of Btk by Src Family Tyrosine Kinases," Mol Cell Biol. 16(7):3465-71 (1996).
Herbert, "Phosphorylation of the Cajal Body: Modification in Search of Function," Arch. Biochem. Biophys. 496 (2):69-76 (2010).
Lowry et al., "Role of the PHTH Module in Protein Substrate Recognition by Bruton's Agammaglobulinemia Tyrosine Kinase," J Biol Chem. 276(48):45276-81 (2001).
Rawlings et al., "Mutation of Unique Region of Bruton's Tyrosine Kinase in Immunodeficient XID Mice," Science 261 (5119):358-61 (1993).
Suzuki et al., "PI3K and Btk Differentially Regulate B Cell Antigen Receptor-mediated Signal Transduction," Nat Immunol. 4(3):280-6 (2003).
Tsai et al., "Etk, a Btk Family Tyrosine Kinase, Mediates Cellular Transformation by Linking Src to STAT3 Activation," Mol Cell Biol. 20(6):2043-54 (2000).
Okoh et al., "Pleckstrin Homology Domains of Tec Family Protein Kinases," Biochem Biophys Res Commun. 265(11):151-7 (1999).
Berns et al., "A Large-scale RNAi Screen in Human Cells Identifies New Components of the p53 Pathway," Nature 428(6981):431-7 (2004).
Scherer et al., "Approaches for the Sequence-specific Knockdown of mRNA," Nat Biotechnol 21(12):1457-65 (2003).
Zhang et al., Targeted Gene Silencing by Small Interfering RNA-based Knock-down Technology, Curr Pharm Biotechnol 5(1):1-7 (2004).
Bertrand et al., "Comparison of Antisense Oligonucleotides and siRNAs in Cell Culture and in vivo," Biochem Biophys Res Commun 296(4):1000-4 (2002).
Wang et al., "Identification of Candidate Predictive and Surrogate Molecular Markers for Dasatinib in Prostate Cancer: Rationale for Patient Selection and Efficacy Monitoring," Genome Biol 8(11):R255 (2007).
Wykosky et al., "A Novel, Potent, and Specific EphrinA1-based Cytotoxin Against EphA2 Receptor Expressing Tumor Cells," Mol Cancer Ther 6(12 Pt 1):3208-18 (2007).
Chabner and Roberts, "Timeline: Chemotherapy and the war on Cancer," Nat Rev Cancer 5(1):65-72 (2005).
Pasquale, "Eph Receptors and Ephrins in Cancer: Bidirectional Signalling and Beyond," Nat Rev Cancer 10(3):165-80 (2010).
Huang et al., "Identification of Candidate Molecular Markers Predicting Sensitivity in Solid Tumors to Dasatinib: Rationale for Patient Selection," Cancer Res 67(5):2226-38 (2007).
Fabien et al., "A Small Molecule-kinase Interaction Map for Clinical Kinase Inhibitors," Nat Biotechnol 23(3):329-36 (2005).
Benner and Gaucher, "Evolution, Language and Analogy in Functional Genomics," Trends Genet 17(7):414-8 (2001).
Jackson et al., "Noise Amidst the Silence: Off-target Effects of siRNAs?," Trends Genet 20(11):521-4 (2004).
Cheung et al., "Natural Variation in Human Gene Expression Assessed in Lymphoblastoid Cells," Nat Genet 33 (3):422-5 (2003).
Saito-Hisaminato et al., "Genome-wide Profiling of Gene Expression in 29 Normal Human Tissues With a cDNA Microarray," DNA Res 9(2):35-45 (2002).
May, "How Many Species are There on Earth?," Science 241(4872):1441-9 (1988).
Greenbaum et al., "Comparing Protein Abundance and mRNA Expression Levels on a Genomic Scale," Genome Biol 4(9):117 (2003).
Free dictionary online (http://www.thefreedictionary.com/patient, downloaded Sep. 23, 2013).
Lowe et al., "p53 Status and the Efficacy of Cancer Therapy in vivo," Science 266(5186):807-10 (1994).
Dermer, "Another Anniversary for the War on Cancer", Biotechnology 12:320 (1994).
Chabert et al., "Cell Culture of Tumors Alters Endogenous Poly(ADPR)polymerase Expression and Activity," Int J Cancer 53(5):837-42 (1993).
Eastham et al., "Relationships Between Clonogenic Cell Survival, DNA Damage and Chromosomal Radiosensitivity in Nine Human Cervix Carcinoma Cell Lines," Int J Radiat Biol 77(3):295-302 (2001).
Hemann et al., "An Epi-allelic Series of p53 Hypomorphs Created by Stable RNAi Produces Distinct Tumor Phenotypes in vivo," Nat Genet 33(3):396-400 (2003).

(56) References Cited

OTHER PUBLICATIONS

Boyer et al., "Characterization of p53 Wild-type and Null Isogenic Colorectal Cancer Cell Lines Resistant to 5-fluorouracil, Oxaliplatin, and Irinotecan," Clin Cancer Res 10(6):2158-67 (2004).

* cited by examiner

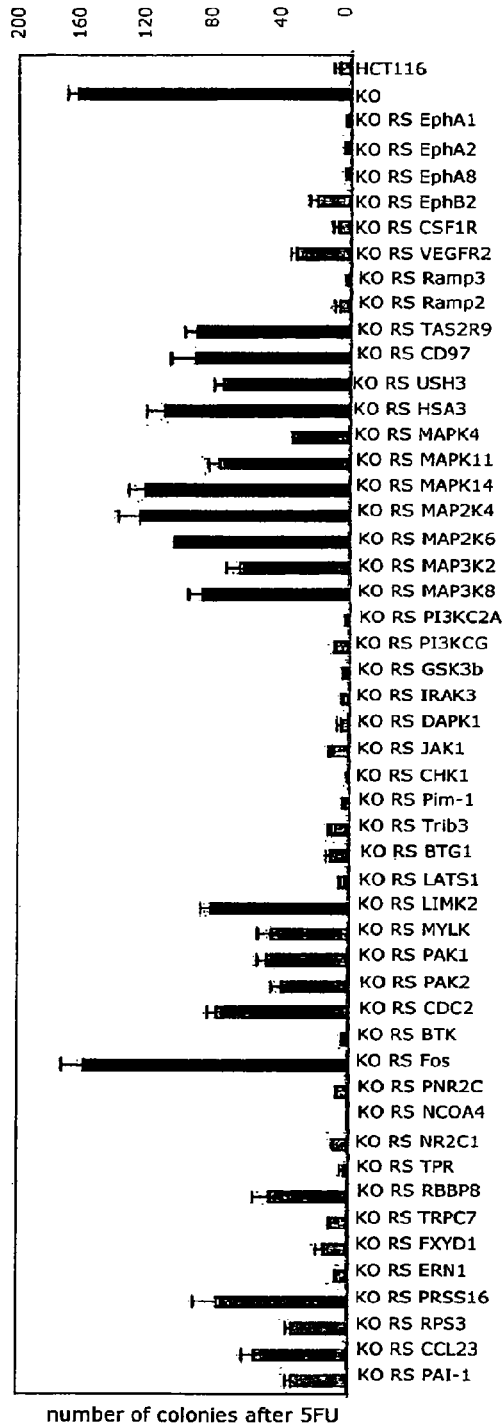
Fig. 1
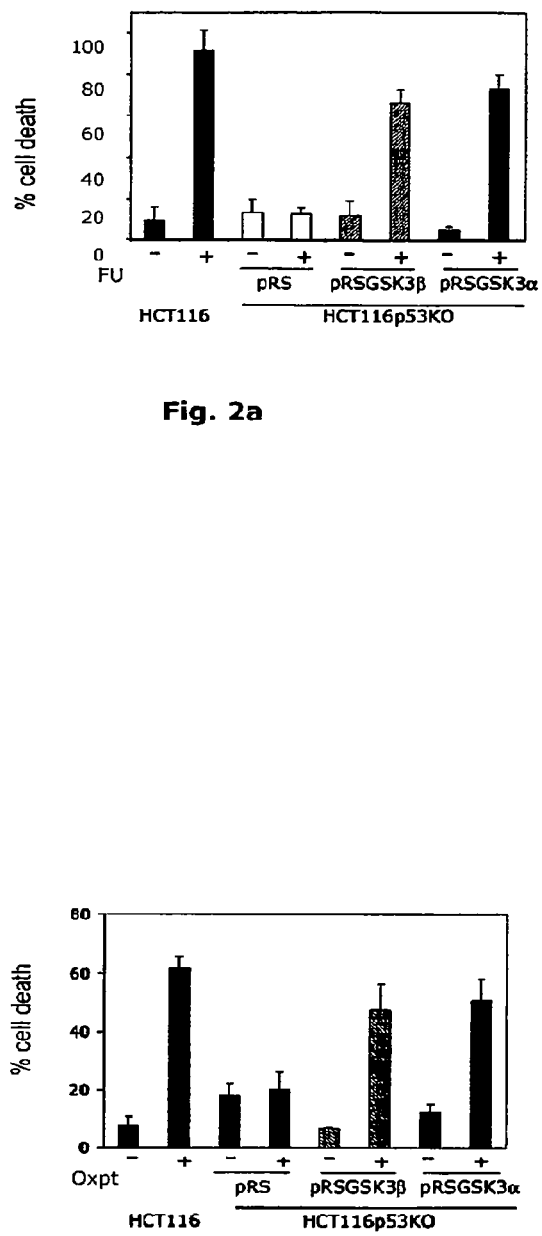
Fig. 2a
Fig. 2b

BLAST EXONS 1-5 NM_000061 vs GENOMIC

BLAST EXONS 1-5 ALTERNATIVE BTK vs GENOMIC

Figure 21
Figure 21c
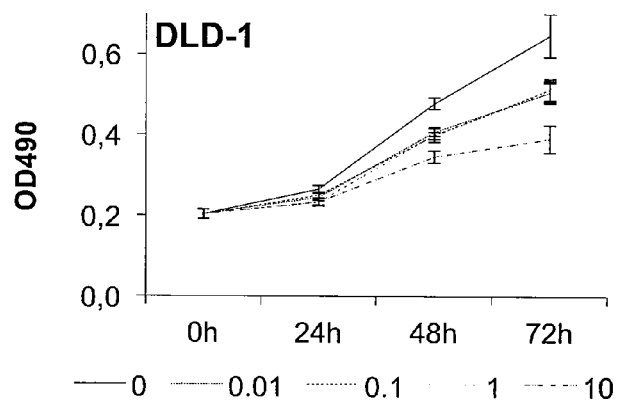
Figure 21d
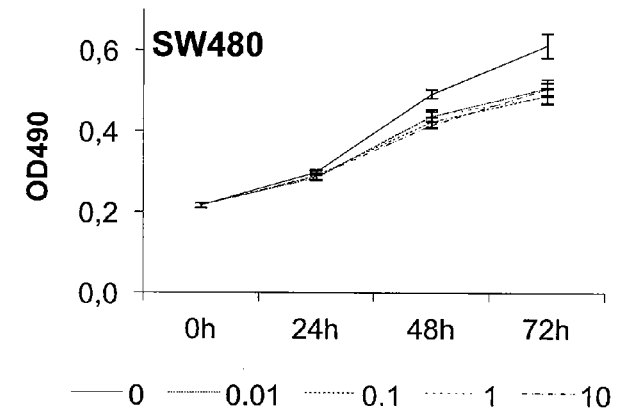

Figure 24
Figure 24a
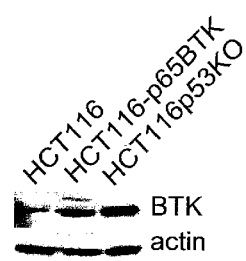
Figure 24b
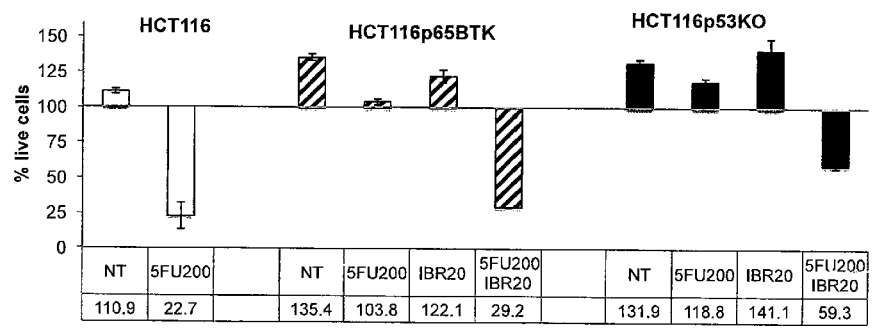

Figure 26
Figure 26a
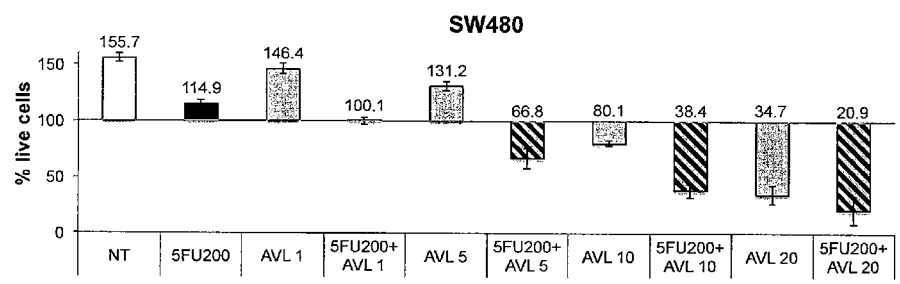
Figure 26b
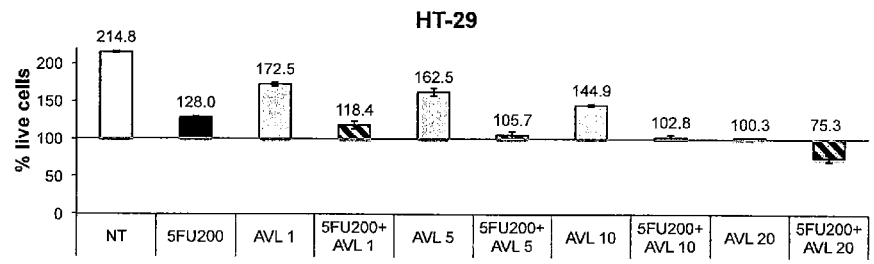

Figure 28
Figure 28a
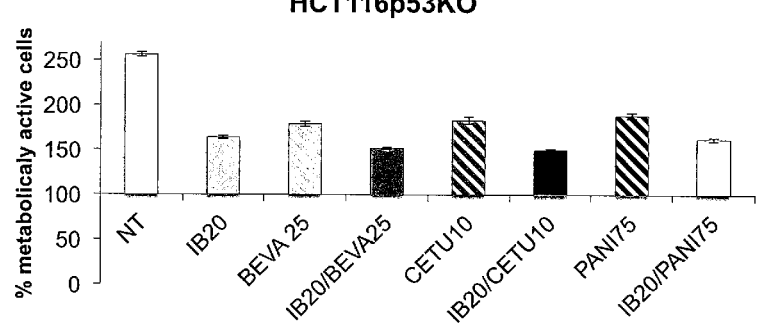
Figure 28b
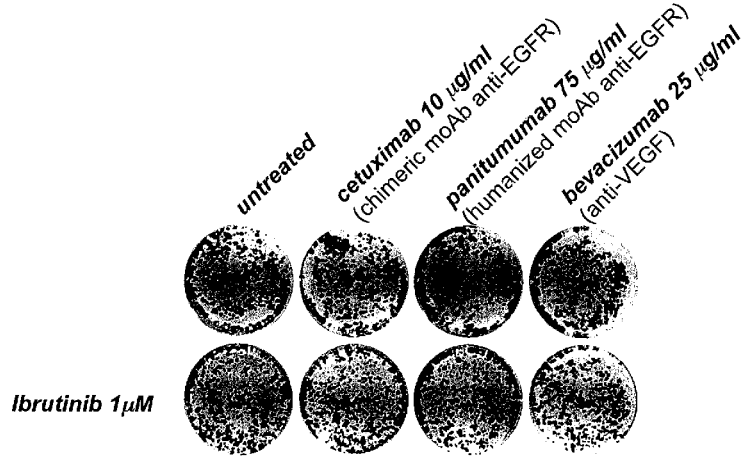

Figure 30
Figure 30a
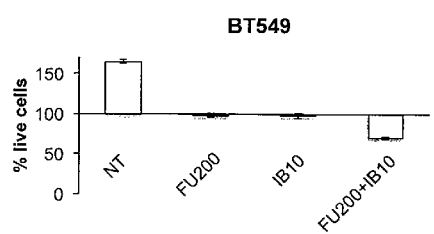
Figure 30b
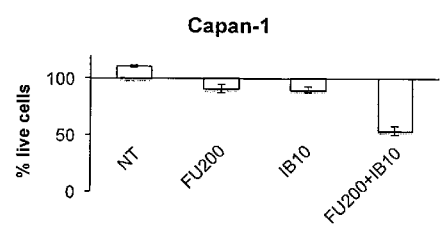
Figure 30c
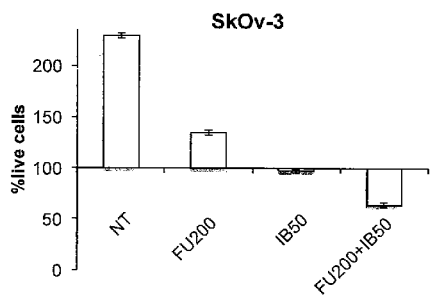

Figure 31
Figure 31a
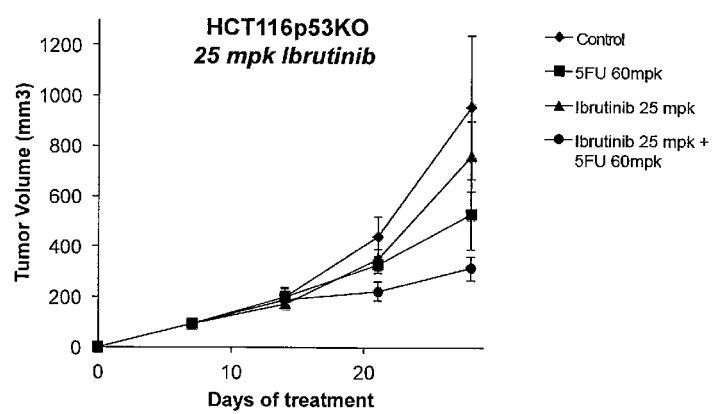
Figure 31b
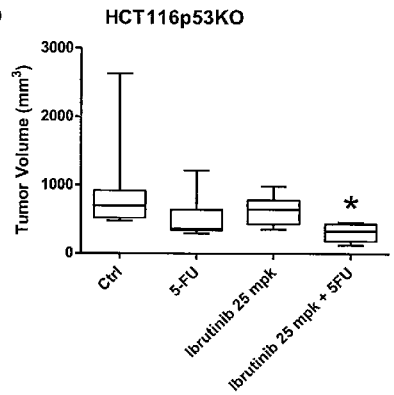
Figure 31c
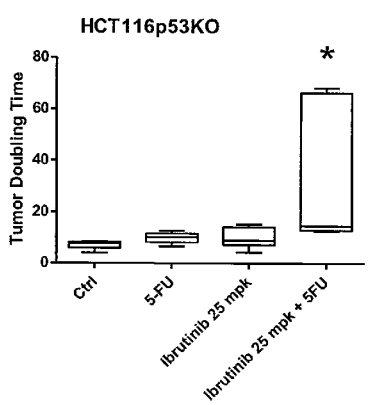

Figure 32
Figure 32a
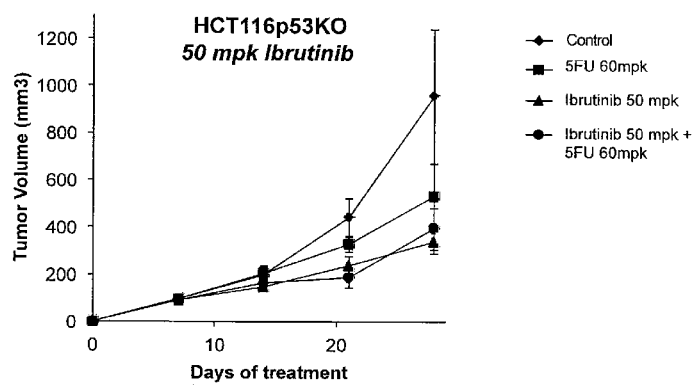
Figure 32b
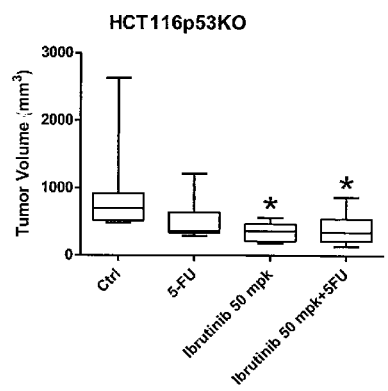
Figure 32c
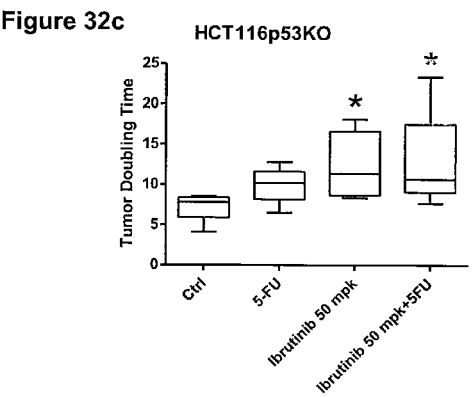

Figure 34
Figure 34a
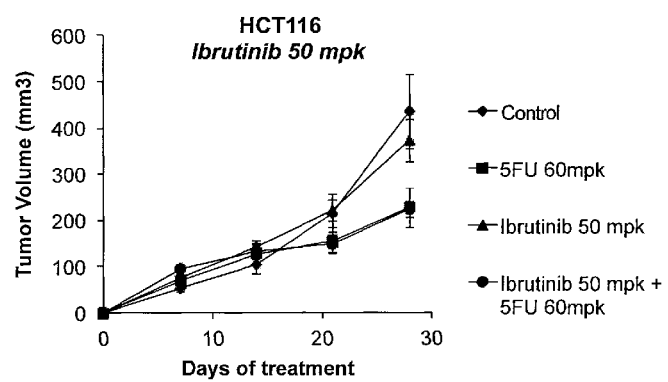
Figure 34b
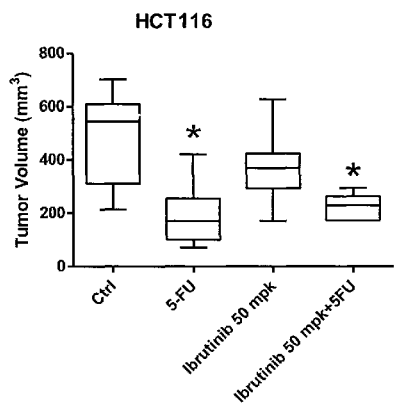
Figure 34c
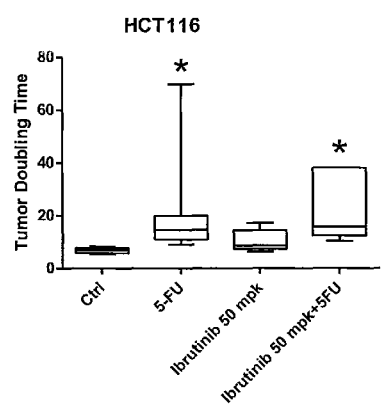

Figure 35
Figure 35a
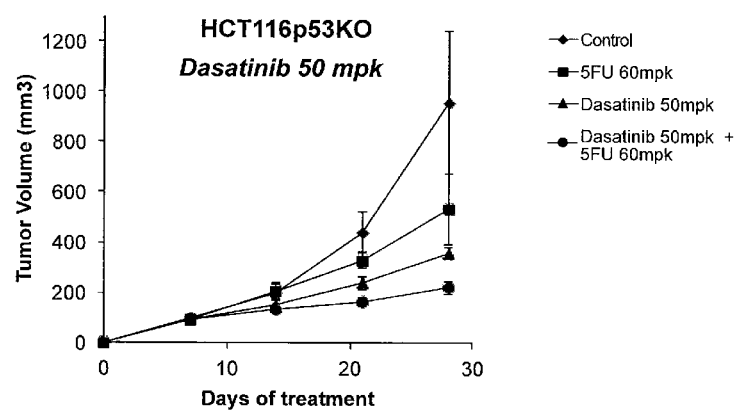
Figure 35b
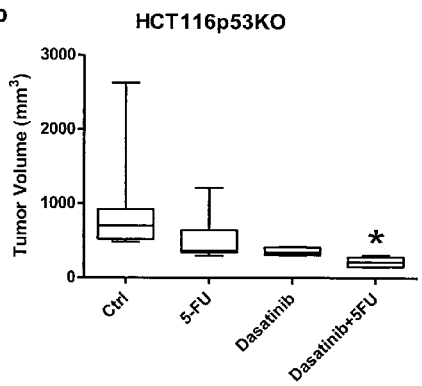
Figure 35c
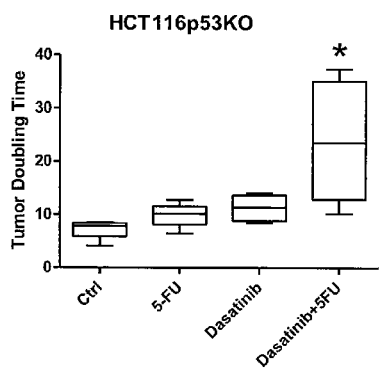

Figure 36
Figure 36a
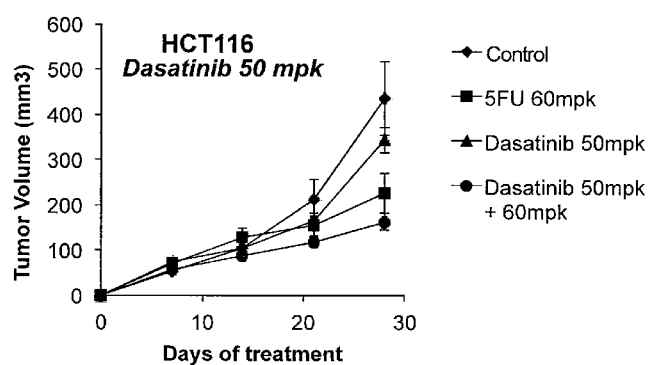
Figure 36b
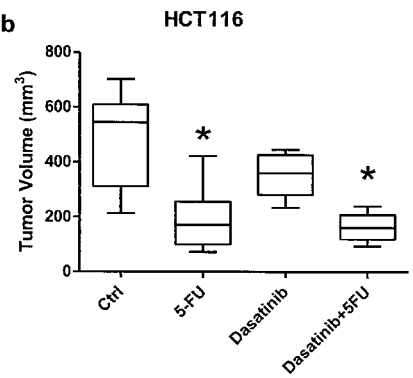
Figure 36c
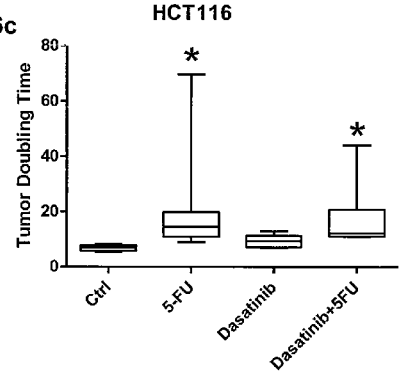

MODULATOR COMPOUNDS OF DRUG RESISTANCE IN EPITHELIAL TUMOR CELLS

CROSS REFERENCE TO RELATED APPLICATIONS

This application is a continuation-in-part of U.S. patent application Ser. No. 14/514,147, filed Oct. 14, 2014, which is a divisional of U.S. patent application Ser. No. 13/532,680, filed Jun. 25, 2012, now U.S. Pat. No. 8,889,643, issued Nov. 18, 2014, which is a divisional of U.S. patent application Ser. No. 12/531,061, filed Sep. 25, 2009, now U.S. Pat. No. 8,232,085, issued Jul. 31, 2012, which is a national stage application under 35 U.S.C. §371 of PCT Application No. PCT/EP08/53099, filed Mar. 14, 2008, which claims priority of Italy Application No. PD2007A000088, filed Mar. 14, 2007, and European Application No. 07106119.6 filed Apr. 13, 2007. The entire content of each of the above-referenced applications is incorporated herein by reference.

FIELD OF THE INVENTION

The present invention relates to the use of compounds for the production of a medicament capable of modulating and diminishing drug resistance in human epithelial tumor cells. It also relates to a method for determining drug resistance in tumor cells as well as a method for the identification of tumor stem cells.

BACKGROUND OF THE INVENTION

One of the most commonly followed strategies in the therapy of neoplastic pathologies foresees the use of several drugs (chemotherapy) belonging to different classes and all acting by induction of the natural process of apoptosis in the tumoral cell.

Nevertheless, it is known that the tumor cells may respond in an unexpected manner to the drug therapy, showing, instead, a strong resistance to the same. It is also known that one of the main reasons for the drug resistance shown by the tumor cells is the incapacity of the cells to begin the process of apoptosis, in response to the chemotherapeutic agent.

A main reason for this, especially when using drugs producing different kinds of DNA damage, is the functional alteration (mutation or deletion) of the gene p53, which is no longer capable of initiating the process of cellular apoptosis in response to DNA damage, thus leading the cells to resist the drug action. The drug resistance levels of the tumor cells can be very high. For example, in the case of tumor cells of the colon-rectum in advanced phase, a therapy based on the antimetabolite and DNA-damaging drug 5-fluorouracil (5FU) shows an effective response only for 10-15% of the cells, and a combination of 5FU with new drugs such as irinotecan and oxaliplatin leads to an increase of the cell mortality up to 40-50%, a value which is still entirely unsatisfactory for an effective therapeutic action towards the neoplastic pathologies.

In recent years, a cell phenomenon was discovered called "RNA interference" (RNAi) by means of which gene expression is silenced in a specific manner. By taking advantage of such process, it is possible to obtain the selective silencing of genes with unknown function, thus permitting the definition of its specific function through the study of the obtained phenotype. By applying RNAi techniques and studying the phenotypic results, it is moreover possible to assign new functions to already known genes.

The genes involved in the phenomenon of drug resistance of the tumor cells are today largely unknown.

There is very much a need, therefore, to identify new genes involved in drug-resistance and to design methods and compounds capable of substantially diminishing the tumor cells' resistance to drugs.

SUMMARY OF THE INVENTION

The problem underlying the present invention is that of making available compounds capable of reducing drug resistance of tumor cells of epithelial type, in order to permit the manufacture of medicaments destined for the therapy of related neoplastic pathologies.

According to one aspect, the described invention provides a method of treating a patient with an epithelial cancer comprising administering a method of treating a patient with an epithelial cancer comprising administering a composition comprising a therapeutic amount of an inhibitor of a BTK protein and one or more chemotherapeutic agent(s) selected from the group consisting of an antimetabolite, a platinum coordination compound, an alkylating agent and a combination thereof, wherein the composition is effective to reduce one or more of tumor cell growth, tumor cell clonogenicity, tumor cell proliferation, tumor cell viability and tumor volume and the therapeutic amount of the inhibitor of a BTK protein and the one or more chemotherapeutic agent(s) exerts a synergistic effect.

According to one embodiment, the inhibitor of a BTK protein is a direct inhibitor or an indirect inhibitor. According to another embodiment, the direct inhibitor is selected from the group consisting of AVL-292, (2Z)-2-cyan-N-(2, 5-dibromophenyl)-3-hydroxy-2-butenamide (LFM-A13), siRNA silencing a BTK gene, ibrutinib and dasatinib. According to another embodiment, the indirect inhibitor is an siRNA silencing a gene selected from the group consisting of EphA1, EphA2, EphA8, EphB2, CSF1R, VEGFR2, RAMP2, RAMP3, CLRN1, MAPK4, PIK3C2A, PIK3CG, GSK3alpha, GSK3beta, IRAK3, DAPK1, JAK1, CHEK1, PIM1, TRB3, BTG1, LATS1, LIMK2, MYLK, PAK1, PAK2, CDC2, PNRC2, NCOA4, NR2C1, TPR, RBBP8, TRPC7, FXYD1, ERN1, PRSS16, RPS3, CCL23, SERPINE1 and a combination thereof. According to another embodiment, the gene is selected from the group consisting of EphA1, EphA2, EphA8, EphB2, CSF1 R, VEGFR2, RAMP2, RAMP3, MAPK4, PIK3C2A, PIK3CG, GSK3 alpha, GSK3beta, IRAK3, DAPK1, JAK1, CHEK1, PIM1, TRB3, BTG1, LATS1, LIMK2, PNRC2, NCOA4, NR2C1, TPR, TRPC7, FXYD1, ERN1, RPS3, SERPINE1 and a combination thereof. According to another embodiment, the gene is selected from the group consisting of EphA1, EphA2, EphA8, RAMP3, PIK3C2A, GSK3alpha, GSK3beta, IRAK3, DAPK1, CHEK1, PIM1, NCOA4, TPR and a combination thereof. According to another embodiment, the gene is selected from the group consisting of GSK3aplpha, GSK3beta and a combination thereof.

According to one embodiment, the chemotherapeutic agent is selected from the group consisting of fluorouracil, oxaliplatin and a combination thereof. According to another embodiment, the antimetabolite is fluorouracil. According to another embodiment, the alkylating agent is oxaliplatin.

According to one embodiment, the epithelial cancer is drug resistant. According to another embodiment, the epithelial cancer has a mutated or deleted p53 gene. According to another embodiment, the epithelial cancer is selected from the group consisting of colon cancer, lung cancer, breast cancer, ovarian cancer, pancreatic cancer, and stomach cancer. According to another embodiment, the epithelial cancer is colon cancer.

According to one embodiment, the BTK protein is of the sequence shown in SEQ ID NO: 2.

According to another aspect, the described invention provides a method of treating a chemotherapy drug-resistant cancer being characterized by increased levels of BTK expression relative to a peritumoral tissue control, comprising administering a therapeutic amount of a small molecule inhibitor of a BTK protein, wherein the therapeutic amount is effective to induce cell death.

According to one embodiment, the small molecule inhibitor is selected from the group consisting of AVL-292, (2Z)-2-cyan-N-(2,5-dibromophenyl)-3-hydroxy-2-butenamide (LFM-A13), siRNA silencing a BTK gene, ibrutinib and dasatinib.

According to one embodiment, the drug-resistant cancer is an epithelial cancer. According to another embodiment, the epithelial cancer has a mutated or deleted p53 gene. According to another embodiment, the epithelial cancer is selected from the group consisting of colon cancer, lung cancer, breast cancer, ovarian cancer, pancreatic cancer, and stomach cancer. According to another embodiment, the epithelial cancer is colon cancer.

According to one embodiment, the BTK protein is of the sequence shown in SEQ ID NO: 2.

According to another aspect, the described invention provides a method of sensitizing a cancer patient to chemotherapy wherein the cancer patient's cells express increased levels of BTK relative to a peritumoral tissue control and are drug resistant, comprising administering a composition comprising a therapeutic amount of a small molecule inhibitor of a BTK protein in combination with a therapeutic amount of one or more chemotherapeutic agent(s), wherein the composition is effective to reduce one or more of tumor cell growth, tumor cell clonogenicity, tumor cell proliferation, tumor cell viability, and tumor volume and the therapeutic effect of the small molecule co-administered with one or more chemotherapeutic agent(s) is synergistic.

According to one embodiment, the small molecule inhibitor is selected from the group consisting of AVL-292, (2Z)-2-cyan-N-(2,5-dibromophenyl)-3-hydroxy-2-butenamide (LFM-A13), siRNA silencing a BTK gene, ibrutinib and dasatinib.

According to one embodiment, the chemotherapeutic agent is selected from the group consisting of fluorouracil, oxaliplatin and a combination thereof.

According to one embodiment, the cells are epithelial cancer cells. According to another embodiment, the epithelial cancer cells are drug resistant. According to anther embodiment, the epithelial cancer cells have a mutated or deleted p53 gene. According to another embodiment, the epithelial cancer cells are selected from the group consisting of colon cancer cells, lung cancer cells, breast cancer cells, ovarian cancer cells, pancreatic cancer cells, and stomach cancer cells. According to anther embodiment, the epithelial cancer cells are colon cancer cells.

According to one embodiment, the BTK protein is of the sequence shown in SEQ ID NO: 2.

According to another aspect, the described invention provides a method of treating a chemotherapy drug-resistant cancer being characterized by increased levels of BTK expression relative to a peritumoral tissue control, comprising co-administering a therapeutic amount of fluorouracil and ibrutinib, wherein the therapeutic amount of the co-administered fluorouracil and ibrutinib has a synergistic effect on reducing tumor volume and increasing tumor doubling time.

According to one embodiment, the drug-resistant cancer is an epithelial cancer. According to another embodiment, where the epithelial cancer has a mutated or deleted p53 gene. According to another embodiment, the epithelial cancer is selected from the group consisting of colon cancer, lung cancer, breast cancer, ovarian cancer, pancreatic cancer, and stomach cancer. According to another embodiment, the epithelial cancer is colon cancer.

According to one embodiment, the BTK protein is of the sequence shown in SEQ ID NO: 2.

BRIEF DESCRIPTION OF THE DRAWINGS

The characteristics and advantages of the invention will be clearer from the detailed description which follows of the tests and results which have led to its definition, reported with reference to the drawing set wherein:

FIG. 1 is a graph illustrating the results of inhibition of the capacity to form drug-resistant tumor cell colonies of the colon treated with the compounds according to the invention and a chemotherapeutic drug.

FIGS. 2a and 2b are graphs showing the results of an analysis of reversion of the resistance of a tumor cell line to two different chemotherapeutic drugs by means of silencing of the alpha and beta isoforms of the gene GSK3.

FIG. 21c: dose-response curve of DLD-1; FIG. 21d: dose-response curve of SW480 cells.

FIG. 24 shows the effect of ibrutinib/5FU combination on viability of drug-sensitive HCT116, HCT116-p65BTK (overexpressing p65BTK upon transfection) and HCT116p53KO drug-resistant colon carcinoma cell lines. FIG. 24a: western blot showing the level of expression of p65BTK in HCT116, HCT116-p65BTK and HCT116p53KO cells; FIG. 24b: the three cell lines were grown in vitro for 72 hs in the presence of different concentrations of 20 μM ibrutinib+200 μM 5FU and their viability was evaluated at the end of the incubation using the calcein assay.

FIG. 26 shows the effect of BTK inhibitor AVL-292 in combination with 5FU on drug-resistant SW480 and HT-29 colon cancer cells. Cells were treated for 72 hrs in absence of any drug or in presence of FU 200 μM; 1 μM AVL-292; 1 μM AVL-292+5FU 200 μM; 5 μM AVL-292; 5 μM AVL-292+5FU 200 μM; 10 μM AVL-292; 100 AVL-292+5FU 2000; 200 AVL-292; 200 AVL-292+5FU 20020 μM; viability was evaluated at the end of the incubation using the calcein assay. FIG. 26a: SW480; FIG. 26b: HT-29.

FIG. 28 shows short- and long-term effects of the combined treatment of ibrutinib and three "targeted" drugs for the inhibition of EGFR (cetuximab, panitumumab) and of VEGF (bevacizumab) on the HCT116p53KO and HCT116 cell lines. FIG. 28a: HCT116p53KO and HCT116 cell lines were grown in vitro for 72 hrs in the presence of 10 μg/ml cetuximab, 75 μg/ml panitumumab, 25 μg/ml bevacizumab±Ibrutinib 20 μM and their viability was evaluated by Trypan blue staining 72 hrs after the combined treatment; FIG. 28b: cells were seeded at low density (1000 cell/each cell line) and grown for 10-12 days in the presence of 10 μg/ml cetuximab, 75 μg/ml panitumumab, 25 μg/ml bevacizumab±Ibrutinib 20 μM and drug containing-medium replaced each 2 days and at the end of the treatment colonies were visualized by crystal violet staining.

FIG. 30 shows effects of the combined treatment of 5FU, ibrutinib and the combination 5FU/Ibrutinib on drug-resistant epithelial cancer cells derived from tumors other than colon. Carcinoma cells were left untreated or treated with 200 μM 5FU or 10 μM (BT549, Capan-1) or 50 μM (SkOv-3) ibrutinib or the combination of the two. Percentage of viable cells was evaluated after 72 hrs of treatment by MTT assay. FIG. 30a: BT549 breast carcinoma cells; FIG. 30b: Capan-1 pancreatic carcinoma cells; FIG. 30c: SK-Ov-3 ovarian carcinoma cells.

FIG. 31 shows kinetics of growth and volumes of HCT116p53KO xenografts upon treatment with 5FU, Ibrutinib low-dose (25 mpk) and combination thereof. FIG. 31a: growth curve of tumors derived from HCT116p53KO cells xenografted in CD1 mice treated with Ibrutinib (25 mpk), 5FU (60 mpk), Ibrutinib (25 mpk)+5FU (60 mpk) and vehicle alone; FIG. 31b: range of tumor volumes measured at the end of the treatment of the mice xenografted with HCT116p53KO cells with Ibrutinib (25 mpk), 5FU (60 mpk), Ibrutinib (25 mpk)+5FU (60 mpk), and vehicle alone (ctrl); FIG. 31c: tumor doubling time measured at the end of the treatment of the mice xenografted with HCT116p53KO cells with Ibrutinib (25 mpk), 5FU (60 mpk), Ibrutinib (25 mpk)+5FU (60 mpk), and vehicle alone (ctrl). The bold line indicates the median of the values, the box indicates the first and third quartile. The maximum and minimum values for each group are also reported.

FIG. 32 shows kinetics of growth and volumes of HCT116p53KO xenografts upon treatment with 5FU, Ibrutinib low-dose (50 mpk) and combination thereof. FIG. 32a: growth curve of tumors derived from HCT116p53KO cells xenografted in CD1 mice treated with Ibrutinib (50 mpk), 5FU (60 mpk), Ibrutinib (50 mpk)+5FU (60 mpk) and vehicle alone; FIG. 32b: range of tumor volumes measured at the end of the treatment of the mice xenografted with HCT116p53KO cells with Ibrutinib (50 mpk), 5FU (60 mpk), Ibrutinib (50 mpk)+5FU (60 mpk), and vehicle alone (ctrl); FIG. 32c: tumor doubling time measured at the end of the treatment of the mice xenografted with HCT116p53KO cells with Ibrutinib 50 mpk), 5FU (60 mpk), Ibrutinib (50 mpk)+5FU (60 mpk), and vehicle alone (ctrl). The bold line indicates the median of the values, the box indicates the first and third quartile. The maximum and minimum values for each group are also reported.

FIG. 34 shows kinetics of growth and volumes of HCT116 xenografts upon treatment with 5FU, Ibrutinib low-dose (50 mpk) and combination thereof. FIG. 34a: growth curve of tumors derived from HCT116 cells xenografted in CD1 mice treated with Ibrutinib (50 mpk), 5FU (60 mpk), Ibrutinib (50 mpk)+5FU (60 mpk) and vehicle alone; FIG. 34b: range of tumor volumes measured at the end of the treatment of the mice xenografted with HCT116 cells with Ibrutinib (50 mpk), 5FU (60 mpk), Ibrutinib (50 mpk)+5FU (60 mpk), and vehicle alone (ctrl). The bold line indicates the median of the values, the box indicates the first and third quartile. The maximum and minimum values for each group are also reported; FIG. 34c: tumor doubling time measured at the end of the treatment of the mice xenografted with HCT116 cells with Ibrutinib 50 mpk), 5FU (60 mpk), Ibrutinib (50 mpk)+5FU (60 mpk), and vehicle alone (ctrl). The bold line indicates the median of the values, the box indicates the first and third quartile. The maximum and minimum values for each group are also reported.

FIG. 35 shows kinetics of growth and volumes of HCT116p53KO xenografts upon treatment with 5FU, Dasatinib (50 mpk) and combination thereof. FIG. 35a: growth curve of tumors derived from HCT116p53KO cells xenografted in CD1 mice treated with Dasatinib (50 mpk), 5FU (60 mpk), Dasatinib (50 mpk)+5FU (60 mpk) and vehicle alone; FIG. 35b: range of tumor volumes measured at the end of the treatment of the mice xenografted with HCT116p53KO cells with Dasatinib (50 mpk), 5FU (60 mpk), Dasatinib (50 mpk)+5FU (60 mpk), and vehicle alone (ctrl). The bold line indicates the median of the values, the box indicates the first and third quartile. The maximum and minimum values for each group are also reported; FIG. 35c: tumor doubling time measured at the end of the treatment of the mice xenografted with HCT116p53KO cells with Dasatinib 50 mpk), 5FU (60 mpk), Dasatinib (50 mpk)+5FU (60 mpk), and vehicle alone (ctrl). The bold line indicates the median of the values, the box indicates the first and third quartile. The maximum and minimum values for each group are also reported.

FIG. 36 shows kinetics of growth and volumes of HCT116 xenografts upon treatment with 5FU, Dasatinib (50 mpk) and combination thereof. FIG. 36a: growth curve of tumors derived from HCT116 cells xenografted in CD1 mice treated with Dasatinib (50 mpk), 5FU (60 mpk), Dasatinib (50 mpk)+5FU (60 mpk) and vehicle alone; FIG. 36b: range of tumor volumes measured at the end of the treatment of the mice xenografted with HCT116 cells with Dasatinib (50 mpk), 5FU (60 mpk), Dasatinib (50 mpk)+5FU (60 mpk), and vehicle alone (ctrl); FIG. 36c: tumor doubling time measured at the end of the treatment of the mice xenografted with HCT116 cells with Dasatinib 50 mpk), 5FU (60 mpk), Dasatinib (50 mpk)+5FU (60 mpk), and vehicle alone (ctrl). The bold line indicates the median of the values, the box indicates the first and third quartile. The maximum and minimum values for each group are also reported.

DETAILED DESCRIPTION OF THE INVENTION

Figures 3A, 3B, 3C:
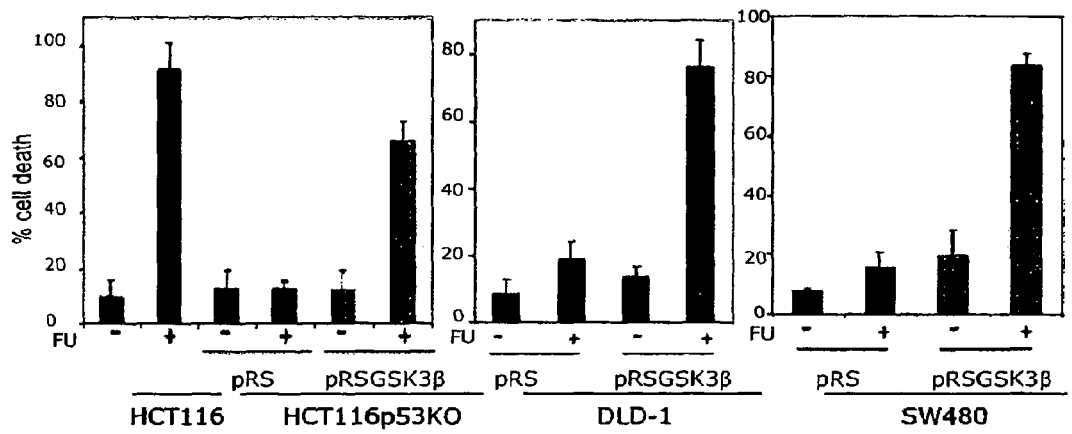
FIGS. 3a-3c are graphs illustrating the results of the tests of reversion of the resistance to a chemotherapeutic drug of three different tumor cell lines of the colon by means of silencing of the gene GSK3beta.

Identification Methodology of the Genes (and Their Products) Modulating Drug Resistance in Epithelial Tumor Cells and Related Validation Tests The above-mentioned technical problem was tackled by subjecting several epithelial tumor cell lines to a series of tests and analyses geared to identify and characterize the genes capable of giving rise to the phenotypic expression of interest, i.e. the reversion of the resistance to the apoptosis induced by chemotherapeutic drugs.

Such identification was conducted by means of phenotypic screening of a representative cell line of the epithelial tumor cells following the selective silencing of an extended group of genes by means of RNAi.

This complex screening work was made possible due to a library of retroviral pRetroSuper (pRS) vectors recently made by the Bernards laboratories. It is known that such vectors are capable of expressing a specific oligonucleotide molecule in a stable manner, known as small interference RNA, in brief siRNA, capable of blocking the translation process of a specific messenger RNA (mRNA) in the corresponding protein. Such mechanism, in brief, foresees that the siRNA molecule (or rather a filament thereof) is associated with the RNA-induced silencing complex (RISC) enzymatic complex, activating it, such that the latter can recognize and bind to the mRNA complementary to the siRNA associated thereto and then degrade it. It follows that the mRNA, identified in a specific manner by the siRNA, cannot be translated in the corresponding amino acid chain, thus obtaining the silencing of the gene from which the mRNA was transcribed. The interference process is specific, so that a siRNA molecule is normally capable of degrading only one mRNA and therefore silencing one single gene. On the other hand, it is instead possible that the same mRNA can be degraded, via RISC, by different siRNA.

This mechanism is one of the different possible modes for functionally blocking a gene (functional knockout). However, the consequent degradation of siRNA via RISC produces only a transient effect on protein levels, thus allowing only short term experiments whose results may be not relevant in the long term. To overcome this problem, short hairpin RNAs (shRNAs), a sequence of RNA folded in the shape of a hairpin, were used as a mechanism for functional knockout. In brief, a vector is used to introduce and incorporate shRNA into the cell chromosome. Transcription of the DNA produces shRNA which is subsequently cleaved by the cellular machinery, DICER, into siRNA. The siRNA then functions as previously mentioned. The incorporation of the shRNA vector into the cell chromosome allows for the gene silencing to be inherited by daughter cells. Thus the usage of shRNAs allows for functional knock out cells that can be used for long term experiments.

It is also known in the literature that the efficiency of transfection for siRNAs is never 100%. Therefore, the use of transfected siRNAs does not assure that all treated cells are successfully deprived of a target protein. The absence of a selectable marker further creates a problem in working with homogeneous populations of cells. Using a selectable marker, such as a puromycin resistance gene, along with a retroviral library, allows for recovery of only the cells bearing shRNAs. Moreover, following shRNA expression selection, only genes whose silencing is compatible with normal cell survival and proliferation are selected for. The absence of these genes does not influence normal cell physiology but only the response to anticancer drugs, a very important consideration while developing anticancer therapy.

The same effect can, in general, be reached by acting in any other step of a gene's protein coding process, such as for example the step of transcription of the gene in mRNA, or the step of mRNA transduction, or by means of inhibition of the protein resulting from the coding process.

The essential and critical step in the resolution of the problem is represented by the identification of the responsible gene or genes of the desired phenotype.

The retroviral library arranged by the Bernards laboratories consists of about 25,000 different elements, capable of silencing about 8,300 genes of the human genome, with a ratio of about 3 different vectors for each gene.

The tests were initially conducted in vitro and subsequently validated ex vivo on different epithelial tumor cell lines, characterized by the lack of or by the mutation of the gene p53 and hence provided with a marked resistance to chemotherapeutic drugs.

In detail, a human RNAi library (NKi library) was established, consisting of 8,300 targeted genes for silencing. The targeted genes included kinases, phosphatases, oncogenes, tumor suppressors, transcription factors, and genes involved in transformation, metastasis, cell cycle, differentiation, apoptosis, metabolic and anabolic processes. A protocol was followed similar to that mentioned in a prior publication (Berns et al., NATURE vol. 428, 25 Mar. 2004). The contents of this publication are incorporated by reference into this application. Briefly, the mRNA sequence for each targeted gene was selected from UniGene. The sequences were masked using RepeatMasker to remove repetitive sequences and searched with NCBI BLAST against UniVec to mask for vector contamination.

Three different 19 nucleotide (19-mer) sequences for silencing each targeted gene were designed, for a total of approximately 25,000 59-mer oligonucleotides that specify short hairpin RNAs (shRNAs). The 19-mer sequences were selected using a selection criteria as mentioned in the Berns publication wherein, a) there were no stretches of four or more consecutive T or A residues (to avoid premature polymerase III transcription termination signals); b) to have 30-70% overall GC content; c) to lie within the coding sequence of the target gene; d) to begin with a G or C residue (consistent with recently established rules for strand bias); e) to begin after an AA dimer in the 5' flanking sequence; f) to end just prior to a TT, TG or GT doublet in the 3' flanking sequence; g) to not contain XhoI or EcoRI restriction enzyme sites to facilitate subsequent shuttling of the knockdown cassette into vector backbones; h) to share minimal sequence identity with other genes; i) to target all transcript variants represented by RefSeq mRNAs; and j) to not overlap with other 19-mers selected from the same target sequence. The 59-mer oligonucleotides were designed so as to contain a 19-mer sequence, its complimentary 19-mer sequence, pol III transcription initiation site, pol III termination site, and HindIII/BglII cloning sites. Utilizing the HindIII/BglII cloning sites, the oligonucleotides were ligated into pRetroSuper (pRS) retroviral vectors, which included a selection cassette for puromycin resistance. The DNA from the three different vectors that targeted the same gene was pooled and virus was produced to infect target cells.

Where a range of values is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, exemplary methods and materials have been described. All publications mentioned herein are incorporated herein by reference to disclose and described the methods and/or materials in connection with which the publications are cited.

It must be noted that as used herein and in the appended claims, the singular forms "a", "and", and "the" include plural references unless the context clearly dictates otherwise.

The publications discussed herein are provided solely for their disclosure prior to the filing date of the present application and each is incorporated by reference in its entirety. Nothing herein is to be construed as an admission that the present invention is not entitled to antedate such publication by virtue of prior invention. Further, the dates of publication provided may be different from the actual publication dates which may need to be independently confirmed.

EXAMPLES

Example 1

The tumor cell line initially used was HCT116p53KO (which differs from the wild type (wt) HCT116 due to the lack of gene p53), related to the colon tumor, while further detailed studies of specific genes were carried out on other drug-resistant tumor cell lines of the colon, such as DLD-1 and SW480, as well as on tumor cell lines of the lung and ovary. In particular, all cell lines that were the object of the analysis, were related to tumors of epithelial type.

Preliminarily, cell lines HCT116p53KO, DLD-1 and SW480 were treated with common chemotherapeutic drugs in order to confirm their resistance to the drug-induced apoptosis.

The chemotherapeutic drugs usable in accordance with the present invention can be of any type suitable for inducing the apoptosis process in the affected tumor cells, such as for example an antimetabolite or any DNA-damaging agent comprising the inhibitors of the topoisomerase I, inhibitors of the topoisomerase II, the platinum coordination compounds and alkylating agents.

The aforesaid preliminary tests have shown that, after treatment for 72 hours in 200 µM 5FU, the cell mortality was less than 10%, against a wt HCT116 cell mortality of greater than 95%.

Supplementary tests of colony forming assays (CFA), have moreover demonstrated that such drug resistance was of non-transitory type. Once the resistance to apoptosis induced by chemotherapeutic drugs was confirmed, $200 \times 10^6$ HCT116p53KO cells were infected with the above-identified pRetroSuper library, provided by the Bernards laboratories. Each vector of this library was advantageously equipped with a selection cassette for a puromycin resistance gene, so that it was possible to select the HCT116p53KO cells actually infected by the vectors of the library through treatment with puromycin (2 mg/l in the culture medium for two days).

At the end of the antibiotic treatment, the still-living cells were then collected, which therefore comprised all of the cells infected by the retroviruses of the library whose silenced genes were not incompatible with cellular survival.

The cells thus collected were then treated with 200 µM 5FU for 72 hours, while at the same time wt HCT116 cells and uninfected HCT116p53KO cells were also subjected to the same treatment, as controls.

At the end of the treatment, it was found that about half of the cells were floating in the culture medium, therefore dead. Such cells represented the sought-after phenotype, so that they were collected and subjected to the necessary treatment for the identification of the genes silenced by the retroviral library.

In brief, such treatments comprised the extraction of the DNA and the amplification by means of PCR (Polymerase Chain Reaction) of a region of 643 base pairs containing the region H1 of a specific promoter and the adjacent region coding the nucleotide sequence of interest. PCR amplification was performed using a pRS-fw primer: 5'-CCCTTGAACCTCCTCGTTCGACC-3' (SEQ ID NO: 4) and pRS-rev primer: 5'-GAGACGTGCTACTTCCATTTGTC-3' (SEQ ID NO: 5). The products obtained by the amplification were then bound in pRS retroviral vectors and the infection process of HCT115p53KO cells was completely repeated with the new vectors, so as to refine the screening. The products were digested with EcoRI/XhoI and recloned into pRS.

The products obtained from the second amplification treatment with PCR on the DNA harvested from the dead cells after new treatment with 5FU were newly isolated and bound in retroviral vectors pRS and then used for transforming DHSalpha bacteria whose respective plasmids were sequenced for the identification of the genes which gave rise to the phenotypic expression of interest.

Once the single genes were obtained and identified whose silencing by means of interference with RNA gave rise to the reversion of the resistance of the tumor cells tested to the 5FU, the separated and independent validation of the single genes took place.

Firstly, the validation was carried out in vitro on HCT116p53KO tumor cell samples, each of which was separately infected with one of the previously-made plasmids, so as to silence in a specific and stable manner one of the genes indicated by the preceding screening and verify its capacity to modulate the resistance to drugs. The samples were then selected with puromycin, placed in Petri dishes at 50% confluence and treated with 200 µM of 5FU for 12 hours.

The evaluation of the reversion of the drug resistance was carried out by means of observation of the formation of colonies according to the protocol defined by the CFA and their comparison with a wt HCT116 sample and an uninfected HCT116p53KO sample.

In FIG. 1, the results obtained from this first in vitro validation are reported in graph form. As shown by the graph, a high percentage of identified genes are capable, when functionally blocked, of consistently reverting the colony forming ability of 5FU-treated HCT116p53KO cells. HCT116 and KO represent positive and negative controls.

This first validation has in particular permitted identifying a group of genes whose specific silencing has given rise to a 5FU-induced inhibition of the growth of the tumor colonies greater than 50% with respect to the HCT116p53KO sample.

These genes, themselves known and characterized, are listed below with their official symbol together with their identification number (between parentheses) reported on the NCBI Entrez Gene data bank: EphA1 (2041), EphA2 (1969), EphA8 (2046), EphB2 (2048), CSF1R (1436), VEGFR2 (3791), RAMP2 (10266), RAMP3 (10268), CLRN1 (7401), MAPK4 (5596), PIK3C2A (5286), PIK3CG (5294), GSK3beta (2932), IRAK3 (11213), DAPK1 (1612), JAK1 (3716), CHEK1 (1111), PIM1 (5292), TRB3 (57761), BTG1 (694), LATS1 (9113), LIMK2 (3985), MYLK (4638), PAK1 (5058), PAK2 (5062), CDC2 (983), BTK (695), PNRC2 (55629), NCOA4 (8031), NR2C1 (7181), TPR (7185), RBBP8 (5932), TRPC7 (57113), FXYD1 (5348), ERN1 (2081), PRSS16 (10279), RPS3 (6188), CCL23 (6368) and SERPINE1 (5054).

Among the above-listed genes, a first subgroup is also identifiable of genes whose silencing advantageously leads to an over 75% inhibition of the tumor cells growth.

Such first subgroup is formed by the following genes: EphA1 (2041), EphA2 (1969), EphA8 (2046), EphB2 (2048), CSF1R (1436), VEGFR2 (3791), RAMP2 (10266), RAMP3 (10268), MAPK4 (5596), PIK3C2A (5286), PIK3CG (5294), GSK3beta (2932), IRAK3 (11213), DAPK1 (1612), JAK1 (3716), CHEK1 (1111), PIM1 (5292), TRB3 (57761), BTG1 (694), LATS1 (9113), LIMK2 (3985), BTK (695), PNRC2 (55629), NCOA4 (8031), NR2C1 (7181), TPR (7185), TRPC7 (57113), FXYD1 (5348), ERN1 (2081), RPS3 (6188) and SERPINE1 (5054).

A second subgroup was further identified of genes whose silencing leads to an over 95% inhibition of the growth of the tumor cells.

Such subgroup is formed by the following genes: EphA1 (2041), EphA2 (1969), EphA8 (2046), RAMP3 (10268), PIK3C2A (5286), GSK3beta (2932), IRAK3 (11213), DAPK1 (1612), CHEK1 (1111), PIM1 (5292), BTK (695), NCOA4 (8031), TPR (7185).

The gene GSKalpha (2931), isoform of the gene GSK3beta, must be added to the above-listed genes; in separate tests whose results are shown by the graphs of FIGS. 2a and 2b it has shown an optimal efficiency in the reversion of the resistance both to 5FU and to the oxaliplatin in HCT116p53KO cells, entirely comparable to its beta isoform. In detail, FIG. 2a compares the percentages of cell deaths in the absence (symbol "−") and presence (symbol "+") of 200 µM 5FU (72 hr treatment) upon wild type (wt) HCT116 cells, HCT116p53KO drug resistant cells, GSK3alpha and GSK3beta silenced gene cells. In comparison to the HCT116p53KO drug resistant cells, HCT116p53KO cells with GSK3alpha and GSK3beta genes silenced resulted in a high percentage of tumor cell death in the presence of 5FU. FIG. 2b compares the percentages of cell deaths in the absence (symbol "−") and presence (symbol "+") of 50 µM oxaliplatin (72 hr treatment) upon wt HCT116 cells, HCT116p53KO drug resistant cells, GSK3alpha and GSK3beta silenced gene cells. In comparison to the HCT116p53KO drug resistant cells, HCT116p53KO cells with GSK3alpha and GSK3beta genes silenced also resulted in a high percentage of tumor cell death in the presence of oxaliplatin.

The formal confirmation of the silencing of the specific genes by means of interference was carried out through Western Blot analysis of the levels of the protein coded by them, if the antibody was commercially available (EphA1, EphA2, CSF1R, VEGFR, GSK3, JAK1, CHEK1, LIMK2, CDC2, BTK). Western Blot analysis was performed by lysing the puromycin-selected cells in E1A buffer (50 mM Hepes pH 8; 500 mM NaCl; 0.1% NP 40; DTT 1 M; EDTA 1 mM). 8-12% SDS-polyacrylamide gel electrophoresis was used to separate 30 µg of protein, which was later transferred to polyvinylidine difluoride membranes. Antibodies were then used to probe the Western Blots.

The effectiveness of the plasmids capable of silencing the genes belonging to the above-identified group was further tested on DLD-1 and SW480, other tumor cell lines of the colon known for possessing mutated p53 and for their resistance to drugs.

The capacity to diminish the resistance to chemotherapeutic drugs was generally confirmed, even with different performances. In particular, the inhibition percentage of the growth of colonies after drug treatment over all three cell lines was optimal when the following genes were silenced: EphA1 (2041), EphA2 (1969), EphA8 (2046), EphB2 (2048), CSF1R (1436), VEGFR2 (3791), PIK3C2A (5286), PIK3CG (5294), GSK3alpha (2931), GSK3beta (2932), IRAK3 (11213), CDC2 (983), CHEK1 (1111), LATS1 (9113), TRB3 (57761), JAK1 (3716), BTK (695), PIM1 (5292), LIMK2 (3985), PAK2 (5062).

Example 2

As an example, in FIGS. 3a-3c graphs are reported following silencing tests of the gene GSK3beta in the three tested tumor cell lines, in which the fraction of dead cells after the treatment with 5FU in samples infected with vectors capable of silencing the aforesaid gene is reported and compared with samples infected with empty vectors. In detail, FIG. 3a compares the percentages of cell deaths in the absence (symbol "−") and presence (symbol "+") of 200 µM 5FU (72 hr treatment) upon wt HCT116 cells, HCT116p53KO drug resistant cells, and GSK3beta silenced gene cells. In comparison to the HCT116p53KO drug resistant cells, HCT116p53KO cells with GSK3beta gene silenced resulted in a high percentage of tumor cell death in the presence of 5FU. FIG. 3b compares the percentages of cell deaths in the absence (symbol "−") and presence (symbol "+") of 200 µM 5FU (72 hr treatment) upon wt DLD-1 cells and GSK3beta silenced gene DLD-1 cells. In comparison to the wt DLD-1 cells, GSK3beta silenced gene DLD-1 cells resulted in a high percentage of tumor cell death in the presence of 5FU. FIG. 3c compares the percentages of cell deaths in the absence (symbol "−") and presence (symbol "+") of 200 µM 5FU (72 hr treatment) upon wt SW480 cells and GSK3beta silenced gene SW480 cells. In comparison to the wt SW480 cells, GSK3beta silenced gene SW480 cells resulted in a high percentage of tumor cell death in the presence of 5FU.

In addition to 5FU, a representative example of the family of chemotherapeutic drugs of the antimetabolic type, the reversion of the resistance to drugs was also tested on chemotherapeutic drugs of different types, such as oxaliplatin.

Figures 4A, 4B:
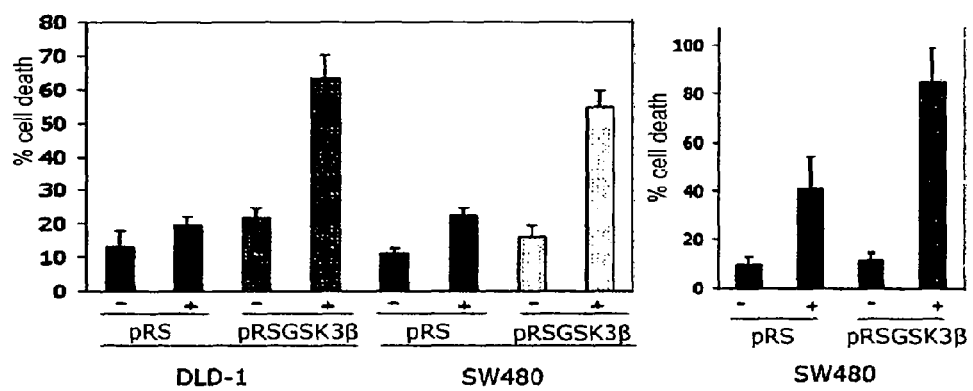
FIG. 4a is a graph illustrating the results of the tests of reversion of the resistance to a different chemotherapeutic drug of two different tumor cell lines of the colon by means of silencing of the gene GSK3beta.
FIG. 4b is a graph illustrating the results of an analysis of reversion of the resistance of a tumor cell line SW480 to the combination of two different chemotherapeutic drugs by means of the silencing of the beta isoform of the gene GSK3.

In FIG. 4a, the fractions of dead cells induced by a treatment with oxaliplatin (50 µM) are reported in samples of colon tumor cell lines DLD-1 and SW480, respectively infected with empty vectors and with vectors silencing the gene GSK3beta.

The substantial diminution of the resistance to the apoptosis induced by oxaliplatin in the sample in which GSK3beta was silenced is evident. In FIG. 4b, a graph is reported in which the results of an analogous test are indicated on the cell line SW480, in which the drug used was a combination of 5FU and oxaliplatin.

As mentioned previously and shown in FIGS. 2a and 2b, GSK3alpha silencing has the same effect as GSK3beta in modulating the apoptotic response to 5FU and oxaliplatin.

Figure 5:
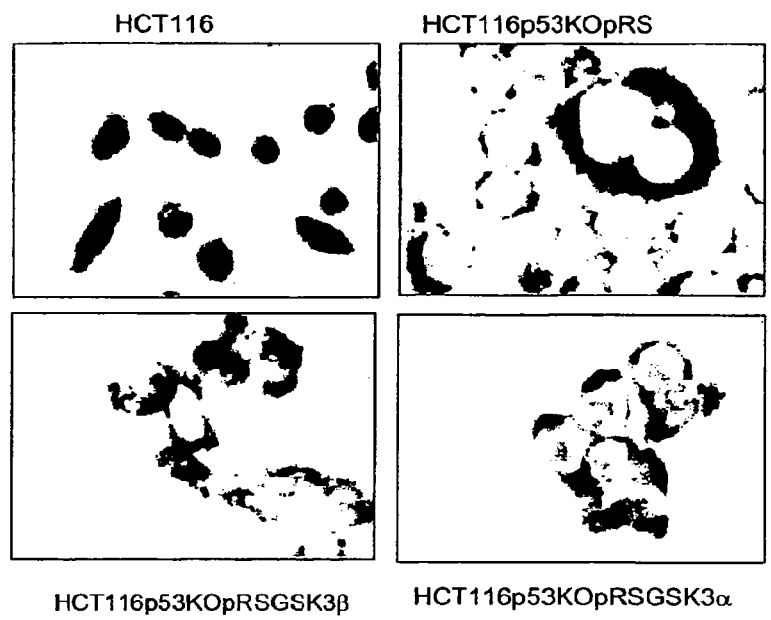
FIG. 5 is a collection of images illustrating the location of cytochrome C for 5FU-induced cell death in the absence of GSK3.
Figure 6:
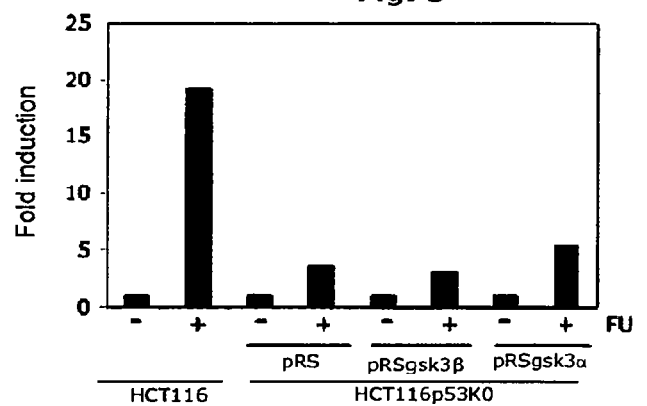
FIG. 6 is a graph illustrating the results of caspase 3 and caspase 7 activation assays in response to 5FU treatment of HCT116 and GSK3alpha, GSK3beta gene silenced HCT116p53KO colon carcinoma cells.
Figure 7:
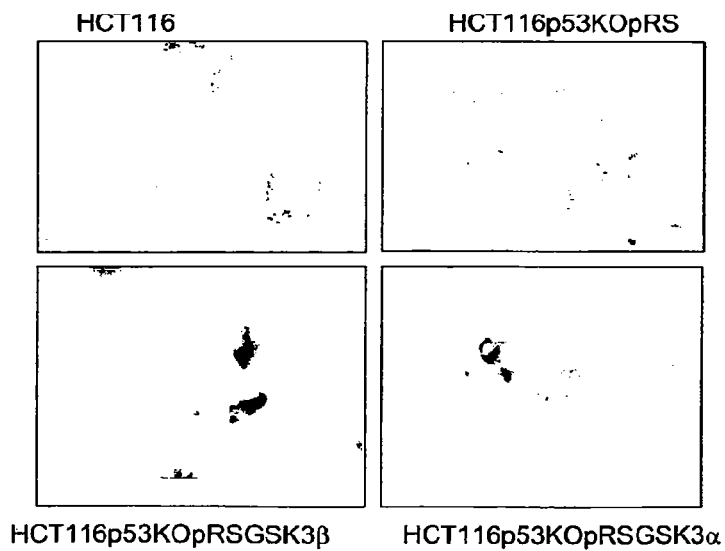
FIG. 7 is a collection of images illustrating the translocation of AIF to the nucleus during 5FU-induced cell death in the absence of GSK3.

Further study was conducted to determine if 5FU-induced cell death in the absence of GSK3 was cytochrome C-dependent or independent. Utilizing anti-cytochrome C and DAPI staining, as shown in FIG. 5, it was found that 5FU-induced cell death in the absence of GSK3 is cytochrome C-independent. More specifically, utilizing anti-AIF and DAPI staining, as shown in FIG. 7, it was discovered that in the absence of GSK3, AIF (apoptosis-inducing factor) translocates to the nucleus resulting in cell death. This was further supported by the finding that caspases 3 and 7 were not activated during 5FU-induced cell death in GSK3 silenced cells, as shown in FIG. 6.

Example 3

Another representative example of the above-identified gene group is constituted by the gene BTK, on which several investigations were undertaken.

BTK kinase is a cytoplasmic protein tyrosine kinase crucial for B-cell development and differentiation. BTK mutation is in fact responsible for X-linked agammaglobulinemia (XLA), a primary immunodeficiency mainly characterized by lack of mature B cells as well as low levels of immunoglobulins. In B cells BTK has been reported as having either pro-apoptotic or anti-apoptotic functions. Moreover, BTK has been so far assumed as being expressed only in some bone marrow-derived lineages such as B and mast cells, erythroid progenitors, platelets. Our finding that BTK is a gene whose silencing reverts resistance to the cytotoxic action of 5FU demonstrated for the first time that BTK is expressed also in cell types others than cells of the hematopoietic lineage. Firstly, the effectiveness was tested of the reversion of the resistance to drugs in HCT116p53KO tumor cells treated with an inhibitor compound of the protein BTK, such to demonstrate how the functional blocking of the gene of interest can be carried out in alternative ways to the silencing by means of RNAi.

The compound employed in these tests was (2Z)-2-cyan-N-(2,5-dibromophenyl)-3-hydroxy-2-butenamide, known as LFM-A13, whose structural formula is reported below in Formula 1.

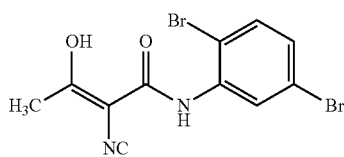

Formula 1

Figure 8:
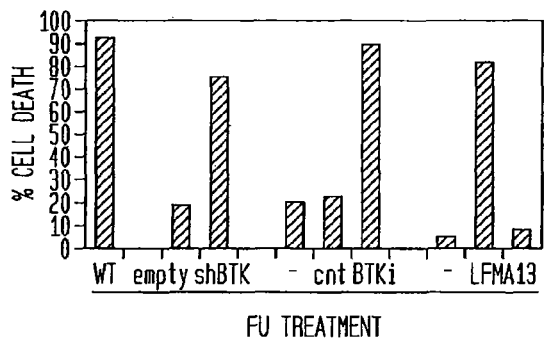
FIG. 8 is a graph illustrating the reversion of the resistance to a chemotherapeutic drug of tumor cell line HCT116p53KO carried out by means of functional blocking of the gene BTK obtained with different methods.

In FIG. 8, the results of the comparison test are reported in a graph of the functional blocking of the BTK gene by means of plasmids (e.g., encoding p68BTK), siRNA or LFM-A13 in samples of HCT116p53KO cells treated with 5FU. The obtained level of reversion to the drug resistance, expressed by means of the percentage fraction of dead cells, for these agents is comparable. In detail, FIG. 8 compares the percentages of cell deaths in the presence of 200 μM 5FU (72 hr treatment) upon wt HCT116 cells and HCT116p53KO drug resistant cells with or without (symbol "empty" and "−") specific depletions of BTK following transient siRNA transfection (symbol "BTKi"), stable retroviral-mediated RNA interference (symbol "shBTK"), and using LFMA13, an inhibitor compound of BTK.

Figure 9:
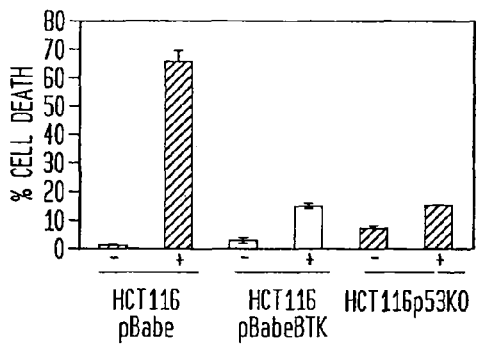
FIG. 9 is a graph illustrating the percentage of cell death induced by 5FU upon BTK overexpression in HCT116 colon carcinoma cells.

According to the protective effect of BTK revealed by the above described inhibition experiments, BTK overexpression protects sensitive HCT116 wt from 5FU-induced cell death. In detail, FIG. 9 compares the percentages of cell deaths in the presence of 200 μM 5FU (72 hr treatment) upon wt HCT116 cells infected with empty pBabe vector, wt HCT116 cells infected with pBabe BTK vector and HCT116p53KO drug resistant cells.

Figure 10A:
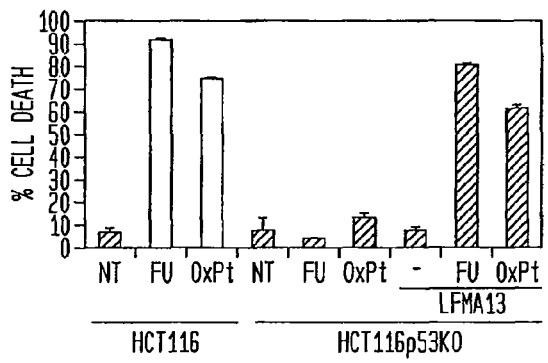
FIGS. 10a and 10b are graphs illustrating the reversion of the resistance to chemotherapeutic drugs by means of the functional blocking of the gene BTK on different colon tumor cell lines.
Figure 10B:
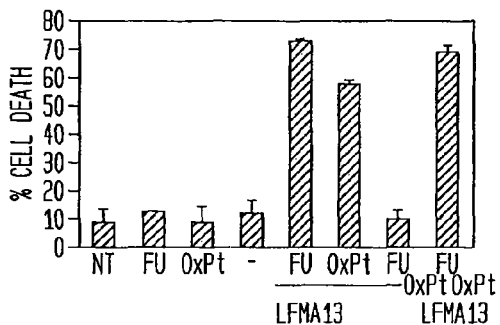

It was also determined that BTK inhibition reverts resistance also to oxaliplatin (FIG. 10a) and in DLD-1 (FIG. 10b).

Figure 11:
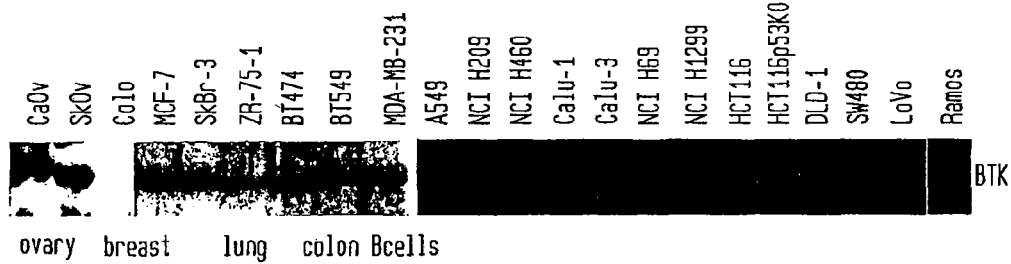
FIG. 11 is a western blot analysis showing BTK expression in several tumoral cell lines derived from different epithelial cancers.

The diminution of the resistance to chemotherapeutic drugs following the functional blocking of the gene BTK by means of LFM-A13 was further confirmed by tests conducted in vitro on epithelial tumor cell lines different from those of the colon. In FIG. 11 levels of BTK have been investigated, by means of Western blot, in several different epithelial carcinoma cell lines showing that the kinase is expressed in most of them. In particular, in FIGS. 12a and 12b, graphs were reported of the reversion tests obtained on SKOV cell lines (related to an ovarian tumor) and A549 cell lines (related to a lung tumor).

Figure 12A:
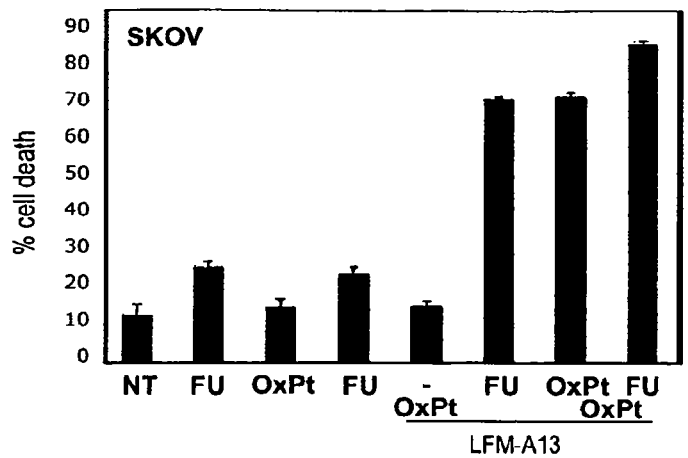
FIGS. 12a and 12b are graphs illustrating the reversion of the resistance to chemotherapeutic drugs by means of the functional blocking of the gene BTK on epithelial tumor cell lines other than colon.
Figure 12B:
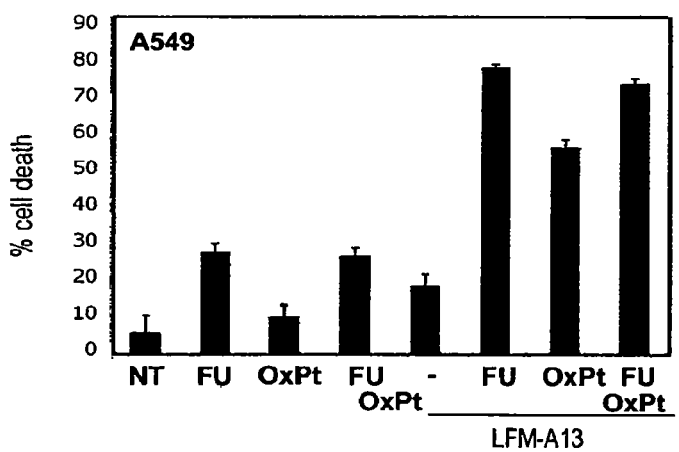

In detail, FIG. 12a compares the percentages of cell deaths in the absence (symbol "NT" and "−") and presence of 200 μM 5FU, 50 μM OxPt, and the combination of the two upon resistant ovarian (SKOV) cells with or without BTK inhibition through the usage of LMFA13. In comparison to the SKOV cells without LMFA13, the SKOV cells with LMFA13 resulted in a high percentage of tumor cell death. FIG. 12b compares the percentages of cell deaths in the absence (symbol "NT" and "−") and presence of 200 μM 5FU, 50 μM OxPt, and the combination of the two upon resistant lung (A549) cells with or without BTK inhibition through the usage of LMFA13. In comparison to the A549 cells without LMFA13, the A549 cells with LMFA13 resulted in a high percentage of tumor cell death.

In both cases, the treatment of the cell lines with LFM-A13, a functional inhibitor of the BTK gene, leads to a considerable increase of the cellular mortality after exposure to 5FU or oxaliplatin or both drugs in combination.

Moreover, the high effectiveness of the action of diminution of the drug-resistance also in these cell lines, confirms that the validity of the results obtained in the preceding tests can be extended more generally to epithelial tumors, such as lung tumor, ovarian tumor and breast tumor.

The results pointed out above have suggested validating the gene BTK also through ex-vivo analysis on epithelial human tumor samples.

Firstly, it was verified through Western Blot that the BTK protein levels were high in 30% of the samples of ovarian tumor cells drawn from patients in advanced stage of disease and/or resistant to chemotherapeutic drugs.

Secondly, examinations were conducted on colon tumor stem cells isolated from patients in order to verify if the investigated genes were expressed (and in what measure) also in this cell type. According to recent studies (Dean et al., 2005), these stem cells would be the responsible principals of the drug resistance.

In all four tumor stem cell lines analyzed, isolated from different patients, the expression of the protein BTK is very high, at least 4-5 times greater than the expression detected on the colon carcinoma cell lines used in the functional experiments, suggesting that the determination of the BTK levels can advantageously be used as a method for defining the stem cell properties of the tumor cells examined, and consequently also their resistance to chemotherapeutic drugs.

Figure 13:
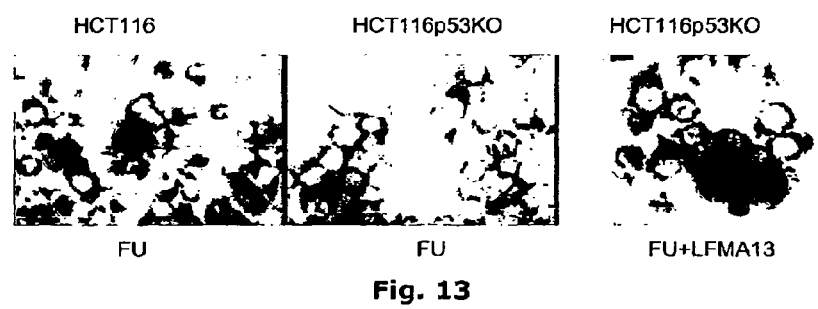
FIG. 13 is collection of images illustrating the cytoplasmic accumulation of cytochrome C in 5FU-treated cells upon BTK inhibition.
Figure 14:
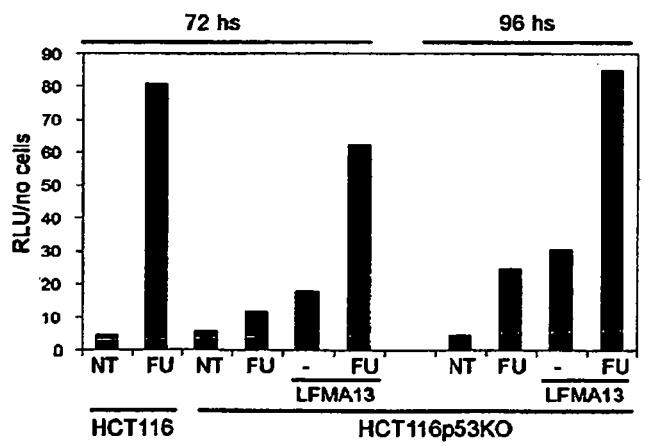
FIG. 14 is a graph illustrating the results of fluorimetric caspase activation assays after 72 hrs and 96 hrs in HCT116 and HCT116p53KO colon carcinoma cells treated with 5FU, BTK inhibition, or the combination of the two.

The results have shown that BTK levels determine the sensitivity of tumor cells to 5FU and that BTK inhibition reverses drug-resistance. Anti-cytochrome C immunostaining in 5FU-treated cells (FIG. 13) showed cytoplasmic accumulation after 5FU treatment in resistant cells only when BTK was inhibited, supporting the finding that reversal of drug-resistance upon BTK inhibition is due to activation of apoptosis. The same finding is also supported by the graph reported in FIG. 14, evaluating the level of caspase 3/7 activation upon 5FU treatment in HCT116p53KO resistant cells in the presence or in the absence of BTK inhibitor LFM-A13. High levels of caspase 3/7 activation, measured by means of a luminometric assay as RLU/number of cells, are observed in 5FU-treated HCT116p53KO cells only when BTK is inhibited.

The predicted and reported molecular weight of BTK protein is 77 kDa. The protein identified in western blot as BTK by a specific antibody (sc-1696, from Santa Cruz Biotechnology) in HCT116p53KO and in all other epithelial carcinoma cell lines tested (6 breast cell lines, 3 ovary cell lines, 7 lung cell lines, 5 colon cell lines), in contrast, has an apparent molecular weight around 65-68 kDa (FIG. 11, FIG. 15a) suggesting that in epithelial cell 22 lines a shorter BTK isoform is expressed.

Figures 15A, 15B:
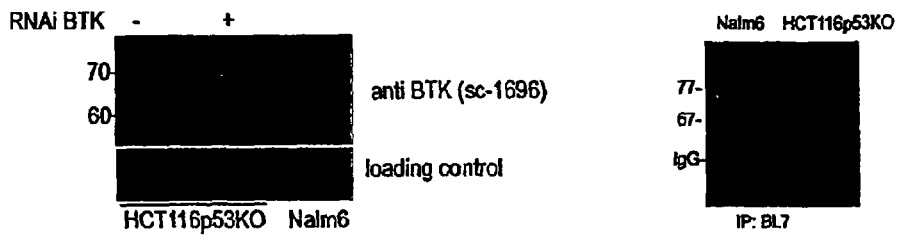
FIG. 15a is a western blot image showing that antibody sc-1696 specifically recognizes BTK protein, that in epithelial carcinoma cells (HCT116p53KO) BTK has an apparent molecular weight of ~67 kDa, and that the same form of the protein is present, together with the "classic" 77 kDa form, also in leukemic cells (Nalm6).
FIG. 15b is an immunoprecipitation-western blot image confirming that a different antibody (BL7) identifies BTK protein as being ~67 kDa in HCT116p53KO cells, and that this isoform is present in leukemic cells (Nalm6) together with the "classic" 77 kDa form.

To confirm these results an immunoprecipitation analysis was carried out using two different and specific BTK antibodies (the above cited sc-1696 and BL7, kind gift of Dr. Mike Tomlinson, University of Birmingham, UK). The results in FIG. 15b show that only this isoform is expressed in epithelial cell lines whereas in a leukemic cell line (Nalm6), already known from the literature to express the classical 77 kDa form, both isoforms are present.

Therefore, a bioinformatic analysis of BTK coding sequence (cds) has been carried out and, accordingly, a second nucleotide triplet ATG (nt 428-430), in frame with the one known to be used to translate BTK (nt 164-166) and susceptible to start the translation of a protein has been identified. The expected molecular weight of the putative protein translated starting from this second ATG is 67 kDa, consistent with the apparent molecular weight of the band identified by different BTK antibodies in epithelial carcinoma cells.

Figure 16:
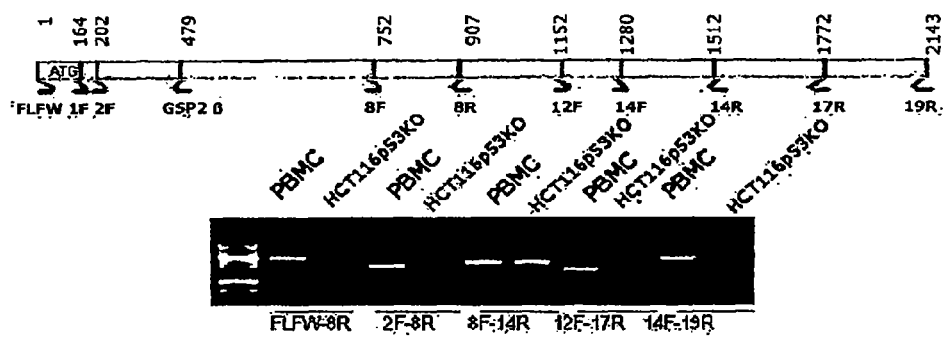
FIG. 16 is an image illustrating the results of a PCR experiment showing that the 5' end upstream of nucleotide 202 in the BTK-encoding mRNA from HCT116p53KO cells is absent or different from the 5' end of BTK mRNA from peripheral blood mononuclear cells (PBMC).

In order to identify which portion is missing in the mRNA coding for the shorter and novel isoform of the BTK protein, PCR experiments using different primers pairs (annealing at different parts of the cds as indicated in the upper diagram of FIG. 16) have been performed. As shown in FIG. 16, these experiments indicate that the 5' end, upstream of nucleotide 202, is absent or different in HCT116p53KO cells.

Figure 17:
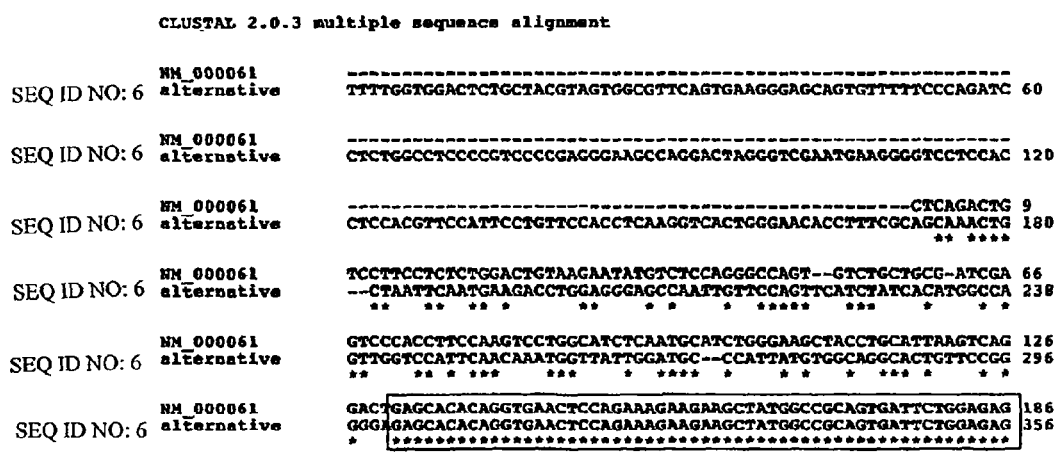
FIG. 17 is an image illustrating the results of ClustalW alignment of BTK transcript, identified by GenBank Accession #NM_000061, and the novel transcript identified in HCT116p53KO cells by 5'RACE PCR followed by cloning and sequencing (indicated as alternative), the box outlining the part of BTK sequence (starting from nucleotide 131 of the known transcript) common between BTK mRNA deriving from #NM_000061 and the novel BTK transcript found in HCT116p53KO.

5'RACE/sequencing experiments have been performed on mRNA from HCT116p53KO cells in order to determine the identity of the unknown 5' end. Subsequently, alignment analysis between the cDNA derived from mRNA from HCT116p53KO cells and the cDNA deriving from the standard BTK mRNA, identified by GenBank accession #NM_000061, using ClustalW computer program (results shown in FIG. 17) demonstrated that the sequence upstream of the second exon (starting at nt 134 of the cds) is different from what reported in literature, i.e., epithelial colon carcinoma cells express a different first exon.

Figure 18:
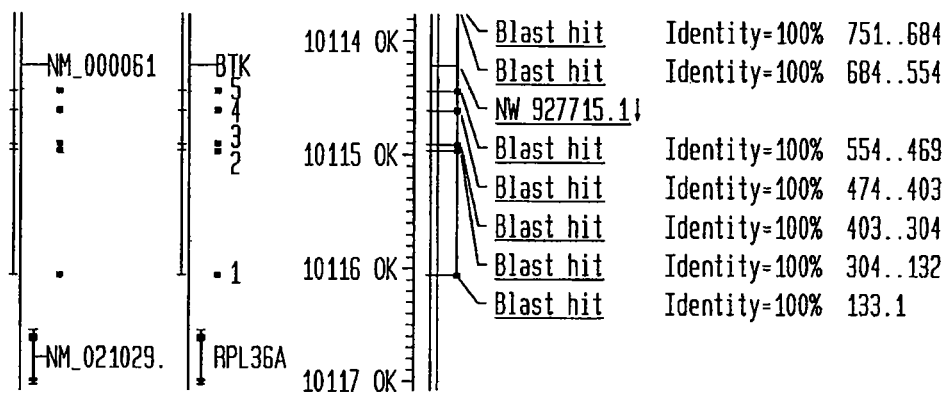
FIG. 18 is an image illustrating the results of a Blast alignment vs a genomic database of exons 1-5 of a BTK transcript identified by GenBank Accession # NM_000061 and the same exons of the novel BTK transcript, the dots indicating the position on chromosome X of the different exons of BTK.
Figure 18:
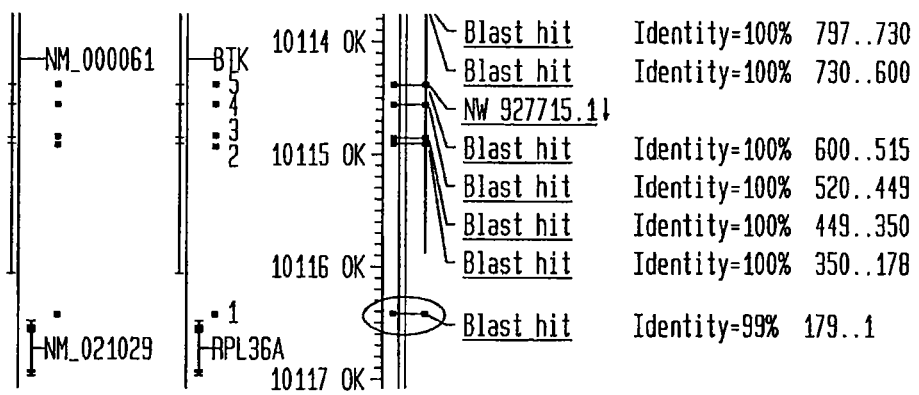

BLAST analysis using a genomic database (FIG. 18) localize the first exon of NM_000061 BTK transcript at 101160K on the chromosome X contig, in correspondence with the beginning of BTK locus. At variance, the first exon of the novel BTK transcript aligns 15192 by 5' of the first known BTK exon, immediately downstream of the RPL36A locus, suggesting that it corresponds to a hitherto unrecognized BTK exon. Moreover, this novel exon is present in HCT116p53KO instead of the first "classical" exon suggesting that this is an "alternative" first exon, whose usage gives raise to a different BTK mRNA, transcribed in cells expressing this shorter BTK isoform.

Figure 19:
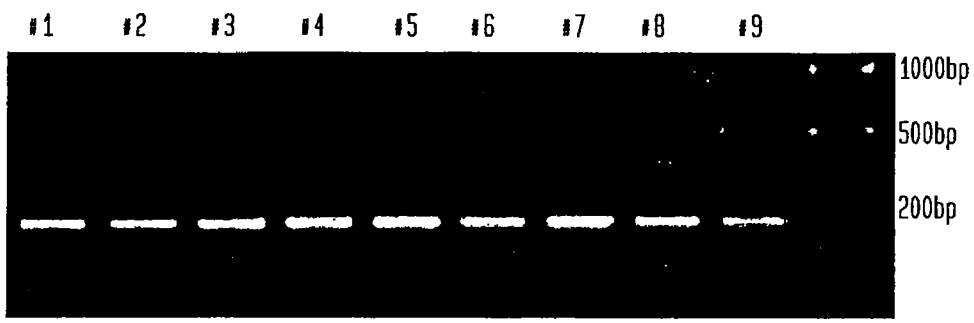
FIG. 19 is an image illustrating the results of a nested PCR experiment showing that the novel BTK transcript is expressed in Formalin-Fixed Paraffin-Embedded (FFPE) tumoral tissues from colon carcinoma patients.

PCR/sequencing experiments demonstrated the expression of this "alternative" BTK mRNA not only in all colon carcinoma cell lines tested (HCT116p53KO, DLD-1 and SW480) but also in 9/9 FFPE-samples from colon carcinoma patients (FIG. 19).

It should be noted that the first exon of BTK, as identified by GenBank accession # NM_000061, corresponds to the 5'UTR of the mRNA, being the ATG triplet encoding the first Met amino acid of BTK protein located in the second exon. 5'UTRs usually perform regulatory functions such as directing cap-dependent or IRES-mediated cap-independent translation. A different first exon, as identified in the novel transcript, can therefore dictate whether a different ATG (in this case an ATG located in the 4th exon) has to be used to start the translation of BTK protein, and therefore regulate the expression of different isoforms.

The nucleotide sequence of the first exon corresponding to the 5'UTR of the novel mRNA expressed by the BTK gene is reported in SEQ ID NO:1, attached to the present description.

The amino acid sequence of the novel isoform of BTK protein coded by the novel transcript is reported in SEQ ID NO:2, attached to the present description (also indicated herein as shBTK and p65BTK).

The above results suggest a method for determining the resistance of tumor cells to chemotherapeutic drugs as well as a method for the identification of the presence of tumor stem cells, wherein the expression of gene BTK comprises the steps of verifying the presence of the novel isoform of the BTK protein.

The presence of the novel isoform of the BTK protein may be controlled by verifying the presence of the protein, for instance using western blot or immunoprecipitation or immunochemistry or immunofluorescence analysis, or, by verifying the presence of the mRNA having the alternative first exon, whose cDNA shows the nucleotide sequence defined in SEQ ID NO:1. The latter may be carried out by means of PCR analysis using primers having a sequence included in SEQ ID NO:1.

This method is expected to show relevant advantages, particularly when used for analyzing tumor tissues taken from human patients.

Actually, it is well known that tumor tissues taken from human patients may contain an effective amount of lymphocytes which may also express BTK protein, thus disturbing the search of BTK protein expressed by the tumor cells.

However, BTK protein expressed by lymphocytes is the "classical" isoform of BTK protein having a molecular weight of 77 KDa, so that the search of the novel isoform of BTK protein may be carried out without any interference, with a simple PCR analysis looking for the presence of BTK mRNA having the alternative first exon.

Example 4

Figure 20:
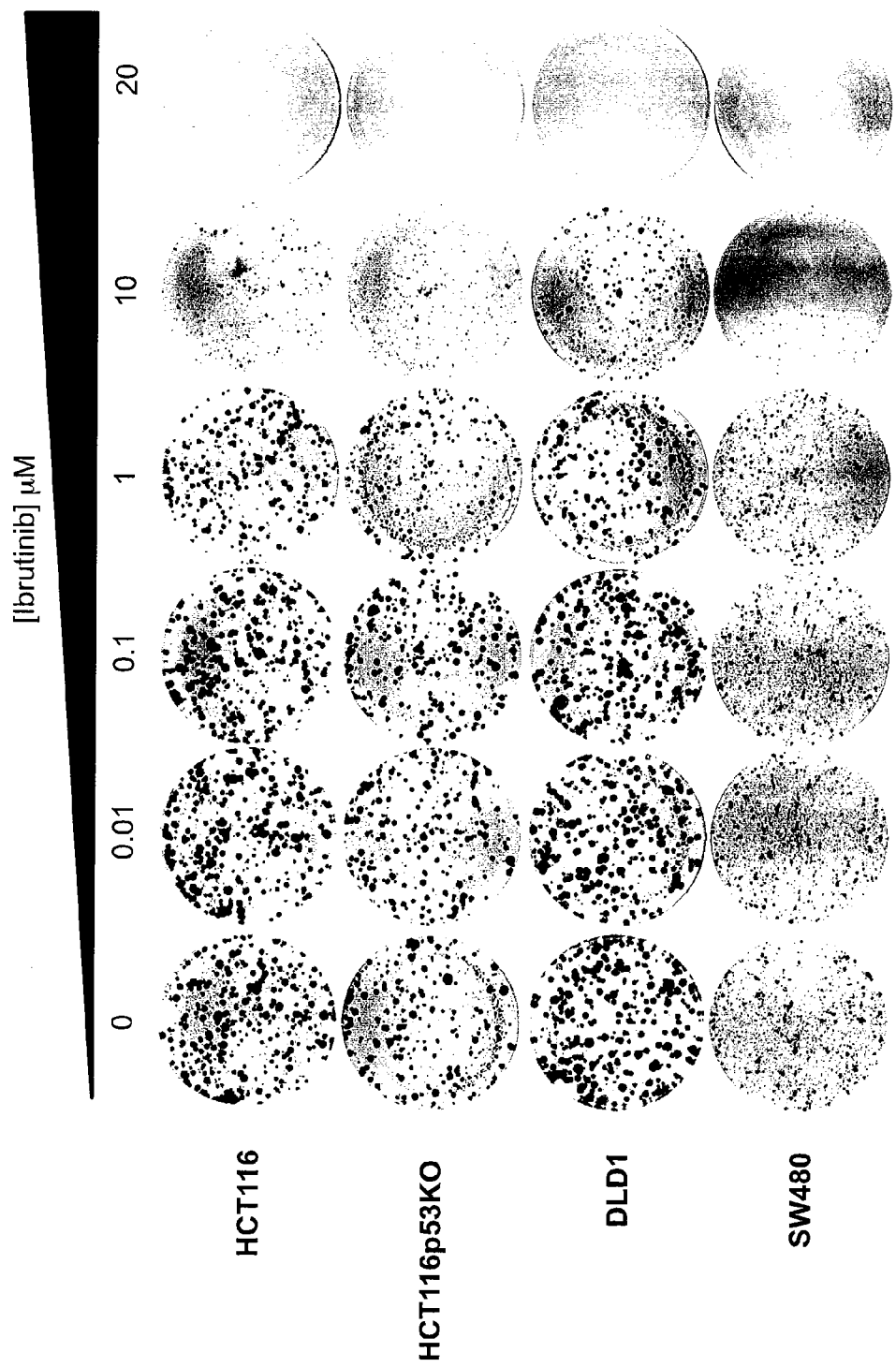
FIG. 20 shows the effect of different concentrations of ibrutinib (from 0 to 20 μM) on cloning efficiency and on the long term proliferation of three colon carcinoma cell lines which are resistant to 5FU (HCT116p53KO, SW480 and DLD-1) and on the sensitive HCT116 cell line. Cells were seeded at low density (1000 cell/each cell line) and grown for 10-12 days in the presence of concentrations of ibrutinib ranging from 0 to 20 μM. Medium was replaced each 3 days and and the end of the treatment colonies were visualized by crystal violet staining.

Effect of Ibrutinib Treatment on the Proliferative Capability and Clonogenicity of Colon Cancer Cells HCT116p53KO, SW480 and DLD-1, three colon carcinoma cell lines which are resistant to 5FU treatment (Grassilli et al, 2013), and HCT116 cell line, which is sensitive to 5FU treatment, were seeded at low density and grown for 10-12 days in the presence of different concentrations of ibrutinib ranging from 0 to 20 µM. As seen in FIG. 20, these long term assays indicated that, on both drug-resistant and drug-sensitive cells, a concentration of 10 µM ibrutinib decreased the number and the size of the colonies indicating that ibrutinib affects both clonogenicity and proliferation, which were eventually inhibited at a concentration of 20 µM. Treatment with ibrutinib does not affect clonogenic and proliferative capabilities up to a concentration of 1 µM.

Example 5

Effect of Ibrutinib Treatment on in vitro Colon Cancer Cells Proliferation

Figures 21, 21A:
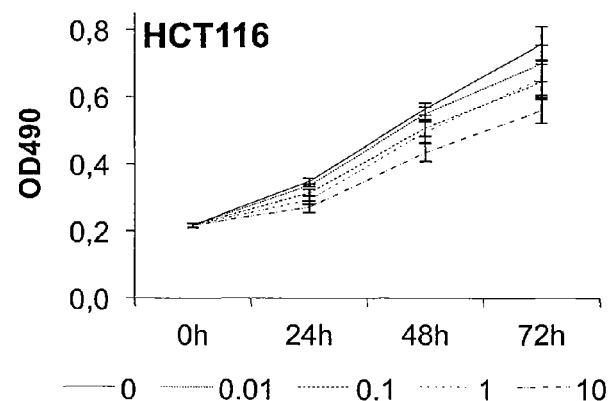
FIG. 21 shows the effect of different concentrations of ibrutinib on cell proliferation. Dose-response proliferation curve of different colon cancer cell lines: cells grown in presence of increasing concentrations of ibrutinib (from 0 to 10 microM) for 72 hours; 5000 cells/well were seeded in triplicates and cell growth was assessed each 24 hrs by use of CellTiter Non-Radioactive Cell Proliferation Assay (Promega).
FIG. 21a: dose-response curve of HCT116 cells.
Figure 21B:
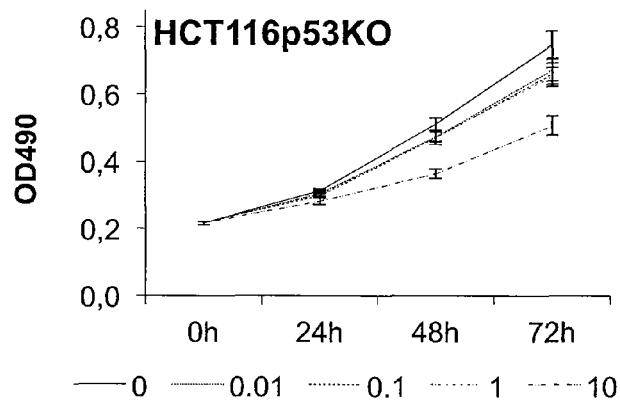
FIG. 21b: dose-response curve of HCT116p53KO cells.

The in vitro proliferation of HCT116p53KO, SW480, DLD-1 and of HCT116 cell lines, were assayed by seeding 5000 cells/well in triplicate and cultivating them in the presence of increasing concentrations of ibrutinib (from 0 to 10 µM), for 72 hours; cell number was assessed every 24 hours by use of CellTiter 96 AQueous Non-Radioactive Cell Proliferation Assay (Promega). As seen in FIG. 21, these short term assays indicated that ibrutinib is not cytotoxic up to a concentration of 10 µM although after 72 hr it slows down the proliferative rate of all cell lines in a dose-dependent manner.

Example 6

Figure 22:
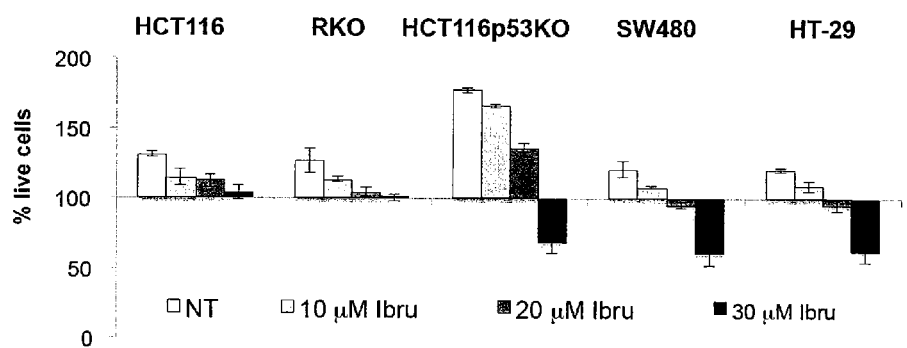
FIG. 22 shows the effect of different concentrations of ibrutinib on cell viability of 5FU drug-resistant, p53-null (HCT116p53KO, SW480 and HT-29) and sensitive, p53 wild type (HCT116, RKO) colon carcinoma cell lines. Cells were grown for 72 hrs in the presence of concentrations of ibrutinib ranging from 0 to 30 μM and viability assessed at the end of the experiment by the calcein assay.

Effect of Ibrutinib in Combination or not with Fluorouracil on Cell Viability of Colon Cancer Cells p53-null 5FU-resistant (HCT116p53KO, SW480 and HT-29) and p53 wild type sensitive (HCT116, RKO) colon carcinoma cell lines were seeded in triplicate (20000 cells/well) and treated with increasing concentrations of ibrutinib (from 0 to 30 µM), for 72 hours; cell viability was evaluated at the end of the incubation using the calcein assay (a non-fluorescent dye that becomes fluorescent upon cleavage by lysosomal esterases; active only in living cells). 100% represent the percentage of living cells at day 0, before starting the treatment. As evident from the graphs shown in FIG. 22, treatment with ibrutinib up to 20 µM decreased the number of cells (relative to non treated cells) in a dose-dependent manner in all cell lines confirming the antiproliferative effect recorded in FIG. 21. At the highest concentration, ibrutinib decreased the number of cells well below 100% only in 5FU-resistant, p53-null (HCT116p53KO, SW480 and HT-29) cell lines indicating that high concentrations of ibrutinib preferentially induce cell death of p53-null cells.

Figure 23:
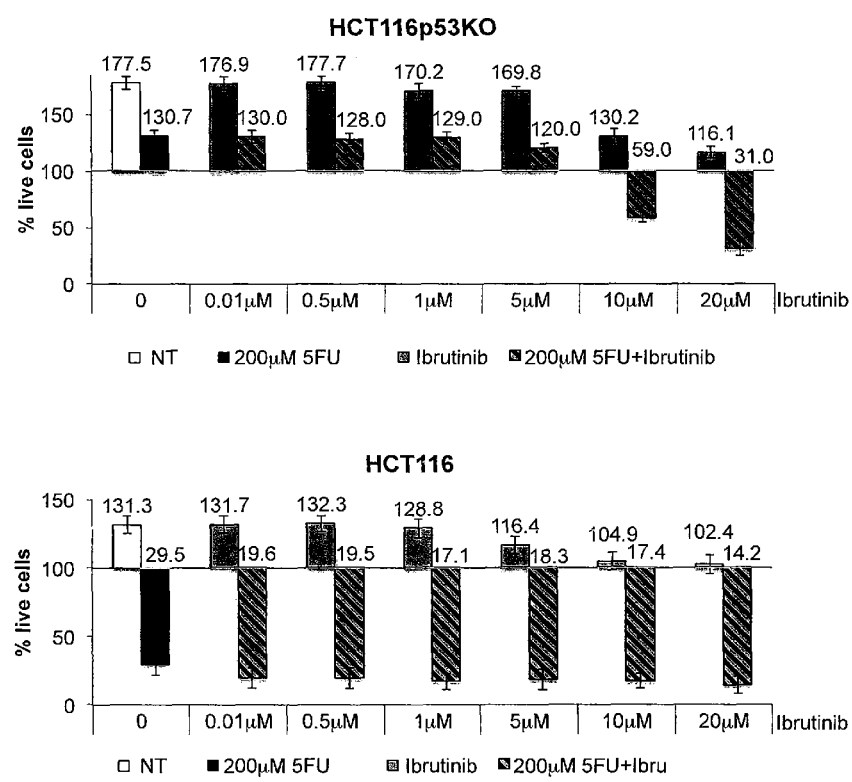
FIG. 23 shows the effect of different concentrations of ibrutinib and ibrutinib+5FU (200 μM) on viability of HCT116 and HCT116p53KO colon carcinoma cell lines. HCT116p53KO and HCT116 cell lines were grown in vitro for 72 hrs in the presence of different concentrations of ibrutinib (from 0 to 20 μM)±5FU (200 μM) and their viability was evaluated at the end of the incubation using the calcein assay.

In FIG. 23, 5FU-resistant HCT116p53KO and 5FU-sensitive HCT116 cell lines were grown in vitro for 72 hr in the presence of different concentrations of ibrutinib (from 0 to 20 µM) and ibrutinib (from 0 to 20 µM)+5FU (200 µM) and their viability was evaluated at the end of the incubation using the calcein assay. 100% represent the percentage of living cells at day 0, before starting the treatment. As seen from the graphs shown in FIG. 23, the percentage of live HCT116p53KO cells did not change after treatment with ibrutinib up to 5 µM and it decreased from 177.5% to 130.2% and 116.1% after treatment with 10 and 20 µM ibrutinib, respectively. 5FU 200 µM alone had also little effect on 5FU-resistant HCT116p53KO; concomitant administration of 5FU and ibrutinib had no synergistic effect up to 10 µM ibrutinib; co-treatment with 5FU+10 or 20 µM ibrutinib induced, 51% and 69% cell death, respectively. Addition of Ibrutinib to 5FU 200 µM in cell cultures of HCT116 (effective dose for sensitive cells) increased only slightly the response to chemotherapy at all concentrations tested.

Figure 25:
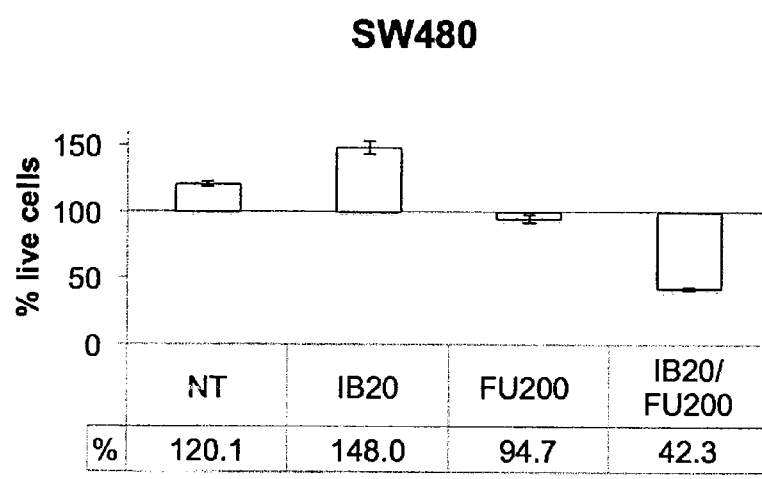
FIG. 25 shows the effect of ibrutinib in combination with 5FU on drug-resistant SW480 colon cancer cells. Cells were treated for 72 hrs in absence of any drug or in presence of 20 μM Ibrutinib; 5FU 200 μM; 20 μM lbrutinib+5FU 200 μM; viability was evaluated at the end of the incubation using the calcein assay.

In FIG. 24 HCT116 drug-sensitive cells, HCT116 overexpressing p65BTK (after transfection with a plasmid encoding p65BTK) and HCT116p53KO 5FU-resistant cells were left untreated or treated with 200 µM 5FU, 20 µM ibrutinib, or a combination thereof. Viability was evaluated after 72 hr of incubation by calcein assay. 100% represent the percentage of living cells at day 0, before starting treatment with the drugs. FIG. 24a, represents a western blot showing the level of expression of p65BTK in HCT116 (characterized by low p65BTK expression), HCT116-p65BTK (HCT116 overexpressing p65BTK upon transfection with a plasmid encoding p65BTK) and HCT116p53KO cells (characterized by high p65BTK expression). As shown in FIG. 24b, HCT116 are sensitive to the cytotoxic effect of 5FU and become resistant, similarly to HCT116p53KO, when overexpressing p65BTK. In both cases 5FU resistance was abolished by concomitant addition of 20 µM ibrutinib. These results validate the concept that increased p65BTK expression correlates with 5FU-resistance and that to abolish 5FU-resistance it is necessary to block p65BTK by ibrutinib or other small molecules targeting BTK. Further support to this concept is given by the data shown in FIG. 25, where 5FU-resistant SW480 colon cancer cells were treated for 72 hr in the absence of any drug or in the presence of ibrutinib 20 µM; 5FU 200 µM; 5FU 200 µM+ibrutinib 20 µM. At the end of the treatment, cell viability was evaluated by calcein assay. 100% represent the percentage of living cells at day 0, before starting treatment with the drugs. Also in this case co-treatment of resistant cells with 5FU and ibrutinib sensitized them to the cytotoxic effect of 5FU.

Example 7

Effect of AVL-292, Another Small Molecule BTK Inhibitor, in Combination or not with Fluorouracil on Cell Viability of Colon Cancer Cells In the experiments shown in FIG. 26 SW480 and HT-29 colon carcinoma cell lines were grown in vitro for 72 hr in the presence of different concentrations of AVL-292, a small molecule inhibitor of BTK, (Celgene Corporation, Summit, N.J.) (from 0 to 20 µM) and of 5FU (200 µM)+AVL-292 (from 0 to 20 µM); cell viability was evaluated at the end of the incubation using the calcein assay. 100% represent the percentage of living cells at day 0, before starting treatment with the drugs. As evident from the graphs, 5FU alone is not cytotoxic but concomitant administration of 200 µM 5FU and AVL-292 sensitize both resistant cell lines to the cytotoxic effect of 5FU. In the case of SW480 cells a concentration of AVL-232 as low as 5 µM, when combined with 200 µM 5FU, is sufficient to induce 66.8% of cell death. Notably, at higher concentrations AVL-292 alone is cytotoxic for SW480 colon cancer cells and induces a dose-dependent increase of cell death from 19.9% at 10 µM to 65.3% at 20 µM (FIG. 26a).

FIG. 26b shows that sensitization of HT-29 cells to the cytotoxic effect of 200 µM 5FU by AVL-292 starts from 20 µM.

Example 8

Figure 27:
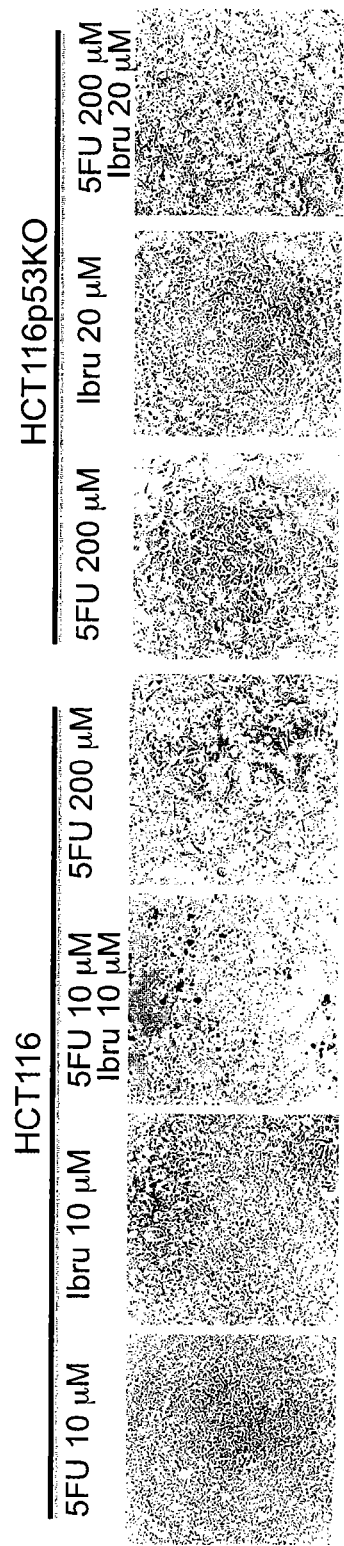
FIG. 27 shows the synergistic effect of singularly ineffective concentrations of 5FU and ibrutinib (Ibru) in drug-sensitive (HCT116) and drug-resistant colon cancer cells (HCT116p53KO). HCT116 and HCT116p53KO cells were treated for 72 hrs in absence of any drug or in presence of 5FU, ibrutinib or 5FU and ibrutinib combined. Photographs were taken at the end of the treatments.

Co-Administration of Ibrutinib Allows the Use of Low Ineffective Concentrations of 5FU to Kill Drug Sensitive Cells FIG. 27a shows representative photographs of sensitive HCT116 cells taken at 72 hr of incubation in the presence of non-toxic concentrations of 5FU and of ibrutinib. When the two drugs are used singularly (10 µM 5FU and 10 µM ibrutinib) no cell death is evident. When the two drugs are used in combination (10 µM 5FU+10 µM ibrutinib) all the cells are detached from the culture dish due to cell death. The fourth picture (5FU 200 µM), shows a culture dish where HCT116 have been treated with the effective concentration of 200 µM of 5FU: massive cell death occurs. The last three pictures on the right, represent drug-resistant HCT116p53KO cells taken at 72 hr of incubation in the presence of 200 µM 5FU and of 20 µM ibrutinib (in both cases no cell death is evident); 200 µM 5FU+20 µM ibrutinib (where cell death is massive).

Example 9

Effect of Ibrutinib on the Response to Targeted Therapy

FIG. 28 illustrates short- and long-term experiments with HCT116p53KO cells treated in vitro, in the presence or in absence of ibrutinib, with three different monoclonal antibodies currently used in anti-cancer therapy for targeting EGFR (cetuximab, panitumumab) and VEGF (bevacizumab), and demonstrates that the co-treatment with ibrutinib does not affect the response to targeted therapy.

Figure 29:
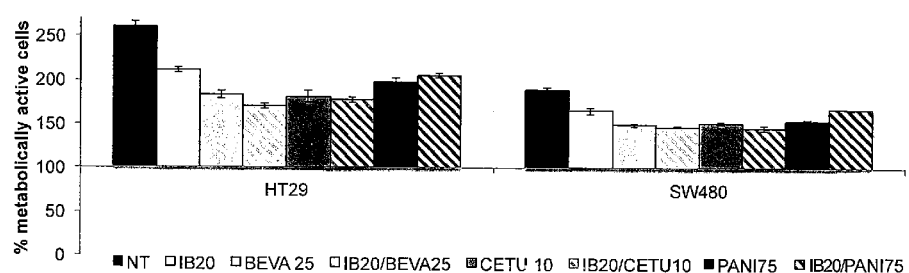
FIG. 29 shows effects of the combined treatment of ibrutinib and three "targeted" drugs for the inhibition of EGFR (cetuximab, panitumumab) and of VEGF (bevacizumab) on the HT29 and SW480 drug-resistant colon carcinoma cell lines. Cells were left untreated or treated with 25 μg/ml bevacizumab or 10 μg/ml cetuximab or 75 μg/ml panitumumab alone or in combination with 20 mM ibrutinib. Percentage of viable cells was evaluated after 72 hrs of treatment by MTT assay.

FIG. 28a shows that treatment with 25 µg/ml bevacizumab, 10 µg/ml cetuximab or 75 µg/ml panitumumab alone does not affect HCT116p53KO cell viability as assessed by MTT assay (a colorimetric assay based on the reduction of tetrazolium salts by enzymes, functioning only in metabolically active, viable cells) 72 hr after the treatment. 100% represent the percentage of living cells at day 0, before starting treatment with the drugs. Targeted therapy slows down the proliferative rate in the short term (FIG. 28a, 72 hr treatment); however, in the long term (FIG. 28b, 2 weeks) the growth of untreated cells and of cells treated with targeted drugs is comparable. Co-treatment with targeted drugs and 20 µM ibrutinib only slightly enhance the decrease of the proliferation of HCT116p53KO cells at 72 hr (FIG. 28a) but do not affect the growth in the long term: in fact cells exposed for 10-12 days to the combined treatment (FIG. 28b) grow as well as untreated cells. In FIG. 29 the same experiment as in FIG. 28a was performed using HT29 and SW480 colon cancer cell lines: also in this case the combination of ibrutinib with targeted drugs did not increase their mild anti-proliferative effect as indicated by the number of metabolically active cells remaining comparable in singularly versus co-treated cells. These results indicate that ibrutinib does not abolish the resistance of colon cancer cells to targeted therapy.

Example 9

Effects of the Combined Treatment of 5FU and Ibrutinib on Drug-Resistant Epithelial Cancer Cells Derived from Tumors Other than Colon BT549 breast cancer cells (FIG. 30a), Capan-1 pancreatic cancer cells (FIG. 30b) and SkOv-3 ovarian carcinoma cells (FIG. 30c) were left untreated or treated with 200 µM 5FU or 10 µM (BT549, Capan-1) or 50 µM (SkOv-3) ibrutinib or the combination of the two. At the end of the treatment, cell viability was evaluated by MTT assay. 100% represent the percentage of living cells at day 0, before starting treatment with the drugs.

As evident from the graphs, in all cases the addition of ibrutinib further and strongly decreased cell viability compared to 5FU alone.

Example 10

In vivo Treatment with Ibrutinib and Fluorouracil

Tumors were established by injecting subcutaneously (s.c.) $1 \times 10^6$ cells (in 100 µL of a 50% PBS and 50% Matrigel solution), drug-resistant HCT116p53KO cells into the left flanks and drug-sensitive HCT116 into the right flanks, of 5 to 7 week old female CD-1 nude mice. When HCT116p53KO tumors reached the average volume of 100 mm$^3$ (day 8 post-engraftment), animals were randomized and given vehicle, 5FU [via intraperitoneal (i.p.) injection, 60 mg/kg, twice a week], ibrutinib [via oral gavage, 25 mg/kg (mpk) or 50 mpk once daily for 5 days a week], or a combination thereof. 5FU treatment started at day 9 post-engraftment, whereas ibrutinib treatment started at day 8 post-engraftment. Control mice received i.p. injections of vehicle (0.9% NaCl solution) with the same schedule as the other groups. Tumors were measured with caliper once a week. Statistical significance was determined with a Kruskal-Wallis nonparametric test (normal distribution not assumable), followed by Nemenyi-Damico-Wolfe-Dunn test for multiple pairwise comparisons between groups. In all cases, a P value <0.05 was considered as significant. Tumor doubling time of xenografts was calculated by using the following algorithm TDT: (Dx-D0)*LOG10 (2)/LOG10 (Vx)-LOG10 (V0), where Dx-D0=days of treatment: Vx: tumor volume at day x of treatment; V0: tumor volume at day 0 (before starting the treatment).

FIG. 31a shows that after 28 days of treatment, the average volume of the tumor masses formed by xenografted drug-resistant HCT116p53KO amounted to ≈955 mm$^3$ for the group of untreated mice (Control); ≈530 mm$^3$ for the group of mice treated with 5FU alone; ≈760 mm$^3$ for the group of mice treated with Ibrutinib (25 mpk) alone; and ≈315 mm$^3$ for the group treated with the combination of 5FU and ibrutinib. As evident from FIG. 31b, 5FU treatment did not cause a significant reduction of the tumor volume as compared to control, whereas the co-treatment with 5FU+ibrutinib reduced tumor volume significantly compared to the untreated group and to the group treated with ibrutinib alone (FIG. 31b, 5FU+Ibr25 Vs. Ctrl, p=0.012, 5FU+Ibr25 Vs. Ibr25, p=0.039). Moreover, the co-treatment with 5FU+ibrutinib (FIG. 31c) also caused a significant increase of the tumor doubling time compared to the untreated group and to the group treated with ibrutinib alone.

FIG. 32a shows that a higher non-toxic dose of ibrutinib (50 mpk) administered to mice did not further decrease the volume of the tumors of the group of mice treated with the combination 5FU+ibrutinib (as compared to the group treated with 5FU+ibrutinib 25 mpk). However, treatment with the higher dose of ibrutinib alone had an anti-tumor effect. FIG. 32b shows that, when compared to the untreated group, the reduction in tumor volume obtained by administering to the mice ibrutinib 50 mpk was as significant as the reduction in tumor volume obtained by administering the combination 5FU+ibrutinib 50 mpk (Ibr50+5FU Vs. Ctrl, p=0.011; Ibr50 Vs. Ctrl, p=0.014). Also the increase of the tumor doubling time of the group treated with ibrutinib 50 mpk was as significant as the increase of the tumor doubling time of the group treated with the combination 5FU+ibrutinib 50 mpk (FIG. 32c).

These results show that the combined treatment of ibrutinib and fluorouracil has a synergistic effect on tumor volume reduction and tumor doubling time when low doses of ibrutinib are administered together with chemotherapy to mice bearing drug-resistant xenografts. In addition, these results show that higher doses of ibrutinib alone have an anti-tumor effect.

Figures 33, 33A:
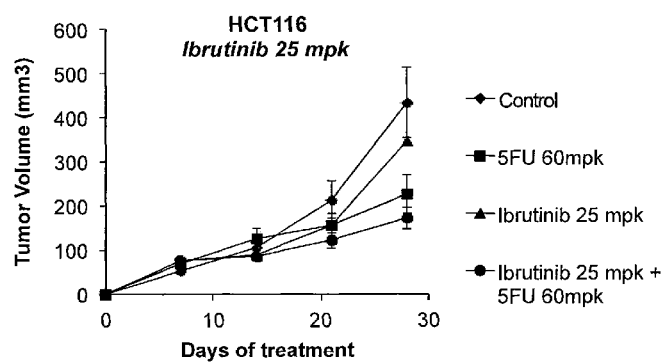
FIG. 33 shows kinetics of growth and volumes of HCT116 xenografts upon treatment with 5FU, Ibrutinib low-dose (25 mpk) and combination thereof.
FIG. 33a: growth curve of tumors derived from HCT116 cells xenografted in CD1 mice treated with Ibrutinib (25 mpk), 5FU (60 mpk), Ibrutinib (25 mpk)+5FU (60 mpk) and vehicle alone.
Figure 33B:
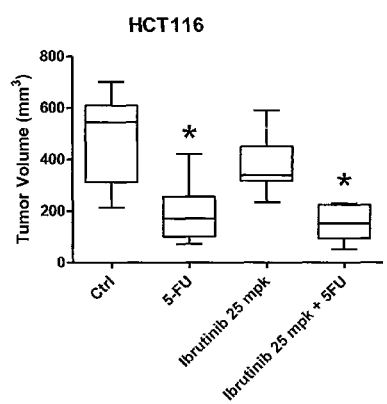
FIG. 33b: range of tumor volumes measured at the end of the treatment of the mice xenografted with HCT116 cells with Ibrutinib (25 mpk), 5FU (60 mpk), Ibrutinib (25 mpk)+5FU (60 mpk), and vehicle alone (ctrl)
Figure 33C:
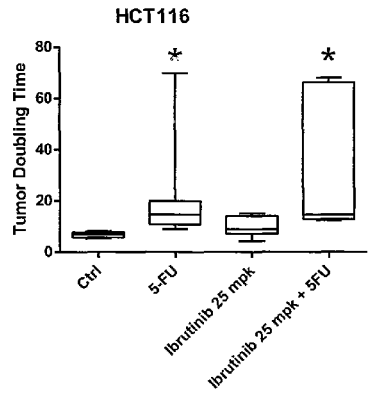
FIG. 33c: tumor doubling time measured at the end of the treatment of the mice xenografted with HCT116 cells with Ibrutinib (25 mpk), 5FU (60 mpk), Ibrutinib (25 mpk)+5FU (60 mpk), and vehicle alone (ctrl). The bold line indicates the median of the values, the box indicates the first and third quartile. The maximum and minimum values for each group are also reported.

FIG. 33a shows the growth curve of tumors derived from HCT116 xenografted in CD1 nude mice after 28 days of treatment with vehicle alone (Control), ibrutinib (25 mpk), 5FU (60 mpk) and 5FU (60 mpk)+ibrutinib (25 mpk). By the end of the treatment, the average volume of the tumor masses formed by xenografted drug-sensitive HCT116 cells amounted to ≈435 mm$^3$ for the group of untreated mice (Control); ≈347 mm$^3$ for the group treated with ibrutinib (25 mpk) alone; ≈226 mm$^3$ for the group treated with 5FU alone; and ≈172 mm$^3$ for the group treated with the combination of 5FU and ibrutinib. Both reduction in the tumor volume (FIG. 33b) and increase of the tumor doubling time (FIG. 33c) were significant when comparing the group of mice treated with 5FU to the untreated (or ibrutinib-treated) group (p<0.05) and co-treatment with ibrutinib did not further decrease tumor volume nor increase the tumor doubling time.

FIG. 34a shows the growth curve of tumors derived from HCT116 xenografted in CD1 nude mice after 28 days of treatment with vehicle alone (Control), ibrutinib (50 mpk), 5FU (60 mpk) and 5FU (60 mpk)+ibrutinib (50 mpk). By the end of the treatment, the average volume of the tumor masses formed by xenografted drug-sensitive HCT116 cells amounted to ≈435 mm$^3$ for the group of untreated mice (Control); ≈372 mm$^3$ for the group treated with Ibrutinib (50 mpk) alone; ≈226 mm$^3$ for the group treated with 5FU alone; and ≈223 mm$^3$ for the group treated with the combination of 5FU and Ibrutinib (FIG. 35a). Both reduction in the tumor volume (FIG. 34b) and increase of the tumor doubling time (FIG. 34c) were significant when comparing the group of mice treated with 5FU to the untreated (or ibrutinib-treated) group (p<0.05) and co-treatment with ibrutinib did not further decrease tumor volume nor increase the tumor doubling time.

These results confirm the growth-reducing effects of 5FU on sensitive xenografts and show that treatment with ibrutinib alone is ineffective against these tumors.

In a different set of in vivo experiments, tumors were established and randomized as described above and then treated with another small molecule drug able to specifically inhibit BTK (i.e., dasatinib). Eight (8) mice per group were treated as follows: with vehicle, with 5FU [via intraperitoneal (i.p.) injection, 60 mg/kg, twice a week], with dasatinib [via oral gavage, 50 mpk once day, for 5 days a week], or a combination thereof. 5FU treatment started at day 9 post-engraftment, whereas dasatinib treatment started at day 8 post-engraftment. Control mice received i.p. injections of vehicle (0.9% NaCl solution) with the same schedule as the other groups. Tumors were measured with caliper once a week. Statistical significance was determined with a Kruskal-Wallis non-parametric test (normal distribution not assumable), followed by Nemenyi-Damico-Wolfe-Dunn test for multiple pairwise comparisons between groups. In all cases, a P value <0.05 was considered as significant After 28 days of treatment, the average volume of the tumor masses formed by xenografted drug-resistant HCT116p53KO amounted to ≈955 mm$^3$ for the group of untreated mice (Control); ≈530 mm$^3$ for the group treated with 5FU alone; ≈355 mm$^3$ for the group treated with dasatinib alone; and ≈218 mm$^3$ for the group treated with the combination of 5FU and dasatinib (FIG. 36a). Reduction in the tumor volume was significant when comparing the group of mice treated with 5FU+dasatinib to the untreated group (Dasa+5FU Vs. Ctrl, p<0.001) and was almost significant (p=0.072) when comparing the group of mice treated with 5FU+dasatinib to the 5FU-treated group (FIG. 36b). Accordingly, also the tumor doubling time was significantly increased in the group of mice treated with 5FU+dasatinib vs control (FIG. 35c).

FIG. 38a, shows the growth curve of tumors derived from HCT116 xenografted in CD1 nude mice after 28 days of treatment with vehicle, 5FU, dasatinib or a combination of 5FU+dasatinib. By the end of the treatment, the average volume of the tumor masses formed by xenografted drug-sensitive HCT116 cells amounted to ≈435 mm$^3$ for the group of untreated mice (Control); 226 mm$^3$ for the group treated with 5FU alone; ≈343 mm$^3$ for the group treated with dasatinib alone; ≈ and ≈163 mm$^3$ for the group treated with the combination of 5FU and dasatinib. Both, reduction in the tumor volume (FIG. 36b) and increase of the tumor doubling time (FIG. 36c) were significant when comparing the group of mice treated with 5FU±dasatinib to the untreated (or dasatinib-treated) group (p<0.05).

These results confirm the growth-reducing effects of 5FU on sensitive xenografts and show that treatment with dasatinib alone is ineffective against these tumors.

The present invention therefore resolves the above-lamented problem with reference to the mentioned prior art, offering at the same time numerous other advantages, including making possible the development of diagnostic methods capable of predicting the therapeutic response so to refine not only the diagnostics but above all direct the best therapeutic choice.

While the present invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the present invention. All such modifications are intended to be within the scope of the claims appended hereto.

What is claimed is:

1. A method of treating a chemotherapy drug-resistant cancer being characterized by increased levels of BTK expression relative to a peritumoral tissue control, comprising administering a therapeutic amount of a small molecule inhibitor of a BTK protein, wherein the therapeutic amount is effective to induce cell death.

2. The method according to claim 1, wherein the small molecule inhibitor is selected from the group consisting of AVL-292, (2Z)-2-cyan-N-(2,5-dibromophenyl)-3-hydroxy-2-butenamide (LFM-A13), siRNA silencing a BTK gene, ibrutinib and dasatinib.

3. The method according to claim 1, wherein the drug-resistant cancer is an epithelial cancer.

4. The method according to claim 3, where the epithelial cancer has a mutated or deleted p53 gene.

5. The method according to claim 3, wherein the epithelial cancer is selected from the group consisting of colon cancer, lung cancer, breast cancer, ovarian cancer, pancreatic cancer, and stomach cancer.

6. The method according to claim 5, wherein the epithelial cancer is colon cancer.

7. The method according to claim 1, wherein the BTK protein is of the sequence shown in SEQ ID NO: 2.

* * * * *

SEQUENCE LISTING

```
<160> NUMBER OF SEQ ID NOS: 6

<210> SEQ ID NO 1
<211> LENGTH: 300
<212> TYPE: DNA
<213> ORGANISM: Homo sapiens

<400> SEQUENCE: 1
ttttggtgga ctctgctacg tagtggcgtt cagtgaaggg agcagtgttt tcccagatc      60 ctctggcctc cccgtccccg agggaagcca ggactagggt cgaatgaagg ggtcctccac    120
```

```
ctccacgttc cattcctgtt ccacctcaag gtcactggga acacctttcg cagcaaactg    180
ctaattcaat gaagacctgg agggagccaa ttgttccagt tcatctatca catggccagt    240
tggtccattc aacaaatggt tattggatgc ccattatgtg gcaggcactg ttccggggga    300
```

<210> SEQ ID NO 2
<211> LENGTH: 571
<212> TYPE: PRT
<213> ORGANISM: Homo sapiens

<400> SEQUENCE: 2

```
Met Glu Gln Ile Ser Ile Ile Glu Arg Phe Pro Tyr Pro Phe Gln Val
1               5                   10                  15

Val Tyr Asp Glu Gly Pro Leu Tyr Val Phe Ser Pro Thr Glu Glu Leu
            20                  25                  30

Arg Lys Arg Trp Ile His Gln Leu Lys Asn Val Ile Arg Tyr Asn Ser
        35                  40                  45

Asp Leu Val Gln Lys Tyr His Pro Cys Phe Trp Ile Asp Gly Gln Tyr
    50                  55                  60

Leu Cys Cys Ser Gln Thr Ala Lys Asn Ala Met Gly Cys Gln Ile Leu
65                  70                  75                  80

Glu Asn Arg Asn Gly Ser Leu Lys Pro Gly Ser His Arg Lys Thr
                85                  90                  95

Lys Lys Pro Leu Pro Pro Thr Pro Glu Glu Asp Gln Ile Leu Lys Lys
            100                 105                 110

Pro Leu Pro Pro Glu Pro Ala Ala Pro Val Ser Thr Ser Glu Leu
        115                 120                 125

Lys Lys Val Val Ala Leu Tyr Asp Tyr Met Pro Met Asn Ala Asn Asp
130                 135                 140

Leu Gln Leu Arg Lys Gly Asp Glu Tyr Phe Ile Leu Glu Glu Ser Asn
145                 150                 155                 160

Leu Pro Trp Trp Arg Ala Arg Asp Lys Asn Gly Gln Glu Gly Tyr Ile
                165                 170                 175

Pro Ser Asn Tyr Val Thr Glu Ala Glu Asp Ser Ile Glu Met Tyr Glu
            180                 185                 190

Trp Tyr Ser Lys His Met Thr Arg Ser Gln Ala Glu Gln Leu Leu Lys
        195                 200                 205

Gln Glu Gly Lys Glu Gly Gly Phe Ile Val Arg Asp Ser Ser Lys Ala
    210                 215                 220

Gly Lys Tyr Thr Val Ser Val Phe Ala Lys Ser Thr Gly Asp Pro Gln
225                 230                 235                 240

Gly Val Ile Arg His Tyr Val Val Cys Ser Thr Pro Gln Ser Gln Tyr
                245                 250                 255

Tyr Leu Ala Glu Lys His Leu Phe Ser Thr Ile Pro Glu Leu Ile Asn
            260                 265                 270

Tyr His Gln His Asn Ser Ala Gly Leu Ile Ser Arg Leu Lys Tyr Pro
        275                 280                 285

Val Ser Gln Gln Asn Lys Asn Ala Pro Ser Thr Ala Gly Leu Gly Tyr
    290                 295                 300

Gly Ser Trp Glu Ile Asp Pro Lys Asp Leu Thr Phe Leu Lys Glu Leu
305                 310                 315                 320

Gly Thr Gly Gln Phe Gly Val Val Lys Tyr Gly Lys Trp Arg Gly Gln
                325                 330                 335

Tyr Asp Val Ala Ile Lys Met Ile Lys Glu Gly Ser Met Ser Glu Asp
            340                 345                 350
```

```
Glu Phe Ile Glu Glu Ala Lys Val Met Met Asn Leu Ser His Glu Lys
            355                 360                 365

Leu Val Gln Leu Tyr Gly Val Cys Thr Lys Gln Arg Pro Ile Phe Ile
    370                 375                 380

Ile Thr Glu Tyr Met Ala Asn Gly Cys Leu Leu Asn Tyr Leu Arg Glu
385                 390                 395                 400

Met Arg His Arg Phe Gln Thr Gln Gln Leu Leu Glu Met Cys Lys Asp
                405                 410                 415

Val Cys Glu Ala Met Glu Tyr Leu Glu Ser Lys Gln Phe Leu His Arg
            420                 425                 430

Asp Leu Ala Ala Arg Asn Cys Leu Val Asn Asp Gln Gly Val Val Lys
        435                 440                 445

Val Ser Asp Phe Gly Leu Ser Arg Tyr Val Leu Asp Asp Glu Tyr Thr
    450                 455                 460

Ser Ser Val Gly Ser Lys Phe Pro Val Arg Trp Ser Pro Pro Glu Val
465                 470                 475                 480

Leu Met Tyr Ser Lys Phe Ser Ser Lys Ser Asp Ile Trp Ala Phe Gly
                485                 490                 495

Val Leu Met Trp Glu Ile Tyr Ser Leu Gly Lys Met Pro Tyr Glu Arg
            500                 505                 510

Phe Thr Asn Ser Glu Thr Ala Glu His Ile Ala Gln Gly Leu Arg Leu
        515                 520                 525

Tyr Arg Pro His Leu Ala Ser Glu Lys Val Tyr Thr Ile Met Tyr Ser
    530                 535                 540

Cys Trp His Glu Lys Ala Asp Glu Arg Pro Thr Phe Lys Ile Leu Leu
545                 550                 555                 560

Ser Asn Ile Leu Asp Val Met Asp Glu Glu Ser
                565                 570

<210> SEQ ID NO 3
<211> LENGTH: 659
<212> TYPE: PRT
<213> ORGANISM: Homo sapiens

<400> SEQUENCE: 3

Met Ala Ala Val Ile Leu Glu Ser Ile Phe Leu Lys Arg Ser Gln Gln
1               5                   10                  15

Lys Lys Lys Thr Ser Pro Leu Asn Phe Lys Lys Arg Leu Phe Leu Leu
            20                  25                  30

Thr Val His Lys Leu Ser Tyr Tyr Glu Tyr Asp Phe Glu Arg Gly Arg
        35                  40                  45

Arg Gly Ser Lys Lys Gly Ser Ile Asp Val Glu Lys Ile Thr Cys Val
    50                  55                  60

Glu Thr Val Val Pro Glu Lys Asn Pro Pro Pro Glu Arg Gln Ile Pro
65                  70                  75                  80

Arg Arg Gly Glu Glu Ser Ser Glu Met Glu Gln Ile Ser Ile Ile Glu
                85                  90                  95

Arg Phe Pro Tyr Pro Phe Gln Val Val Tyr Asp Glu Gly Pro Leu Tyr
            100                 105                 110

Val Phe Ser Pro Thr Glu Glu Leu Arg Lys Arg Trp Ile His Gln Leu
        115                 120                 125

Lys Asn Val Ile Arg Tyr Asn Ser Asp Leu Val Gln Lys Tyr His Pro
    130                 135                 140

Cys Phe Trp Ile Asp Gly Gln Tyr Leu Cys Cys Ser Gln Thr Ala Lys
145                 150                 155                 160
```

```
Asn Ala Met Gly Cys Gln Ile Leu Glu Asn Arg Asn Gly Ser Leu Lys
            165                 170                 175

Pro Gly Ser Ser His Arg Lys Thr Lys Lys Pro Leu Pro Pro Thr Pro
        180                 185                 190

Glu Glu Asp Gln Ile Leu Lys Lys Pro Leu Pro Pro Glu Pro Ala Ala
        195                 200                 205

Ala Pro Val Ser Thr Ser Glu Leu Lys Lys Val Val Ala Leu Tyr Asp
    210                 215                 220

Tyr Met Pro Met Asn Ala Asn Asp Leu Gln Leu Arg Lys Gly Asp Glu
225                 230                 235                 240

Tyr Phe Ile Leu Glu Glu Ser Asn Leu Pro Trp Trp Arg Ala Arg Asp
                245                 250                 255

Lys Asn Gly Gln Glu Gly Tyr Ile Pro Ser Asn Tyr Val Thr Glu Ala
            260                 265                 270

Glu Asp Ser Ile Glu Met Tyr Glu Trp Tyr Ser Lys His Met Thr Arg
        275                 280                 285

Ser Gln Ala Glu Gln Leu Leu Lys Gln Glu Gly Lys Glu Gly Gly Phe
        290                 295                 300

Ile Val Arg Asp Ser Ser Lys Ala Gly Lys Tyr Thr Val Ser Val Phe
305                 310                 315                 320

Ala Lys Ser Thr Gly Asp Pro Gln Gly Val Ile Arg His Tyr Val Val
                325                 330                 335

Cys Ser Thr Pro Gln Ser Gln Tyr Tyr Leu Ala Glu Lys His Leu Phe
            340                 345                 350

Ser Thr Ile Pro Glu Leu Ile Asn Tyr His Gln His Asn Ser Ala Gly
        355                 360                 365

Leu Ile Ser Arg Leu Lys Tyr Pro Val Ser Gln Gln Asn Lys Asn Ala
    370                 375                 380

Pro Ser Thr Ala Gly Leu Gly Tyr Gly Ser Trp Glu Ile Asp Pro Lys
385                 390                 395                 400

Asp Leu Thr Phe Leu Lys Glu Leu Gly Thr Gly Gln Phe Gly Val Val
                405                 410                 415

Lys Tyr Gly Lys Trp Arg Gly Gln Tyr Asp Val Ala Ile Lys Met Ile
            420                 425                 430

Lys Glu Gly Ser Met Ser Glu Asp Glu Phe Ile Glu Glu Ala Lys Val
        435                 440                 445

Met Met Asn Leu Ser His Glu Lys Leu Val Gln Leu Tyr Gly Val Cys
    450                 455                 460

Thr Lys Gln Arg Pro Ile Phe Ile Ile Thr Glu Tyr Met Ala Asn Gly
465                 470                 475                 480

Cys Leu Leu Asn Tyr Leu Arg Glu Met Arg His Arg Phe Gln Thr Gln
                485                 490                 495

Gln Leu Leu Glu Met Cys Lys Asp Val Cys Glu Ala Met Glu Tyr Leu
            500                 505                 510

Glu Ser Lys Gln Phe Leu His Arg Asp Leu Ala Ala Arg Asn Cys Leu
        515                 520                 525

Val Asn Asp Gln Gly Val Val Lys Val Ser Asp Phe Gly Leu Ser Arg
    530                 535                 540

Tyr Val Leu Asp Asp Glu Tyr Thr Ser Ser Val Gly Ser Lys Phe Pro
545                 550                 555                 560

Val Arg Trp Ser Pro Pro Glu Val Leu Met Tyr Ser Lys Phe Ser Ser
                565                 570                 575
```

```
Lys Ser Asp Ile Trp Ala Phe Gly Val Leu Met Trp Glu Ile Tyr Ser
            580                 585                 590

Leu Gly Lys Met Pro Tyr Glu Arg Phe Thr Asn Ser Glu Thr Ala Glu
        595                 600                 605

His Ile Ala Gln Gly Leu Arg Leu Tyr Arg Pro His Leu Ala Ser Glu
    610                 615                 620

Lys Val Tyr Thr Ile Met Tyr Ser Cys Trp His Glu Lys Ala Asp Glu
625                 630                 635                 640

Arg Pro Thr Phe Lys Ile Leu Leu Ser Asn Ile Leu Asp Val Met Asp
                645                 650                 655

Glu Glu Ser

<210> SEQ ID NO 4
<211> LENGTH: 23
<212> TYPE: DNA
<213> ORGANISM: Homo sapiens

<400> SEQUENCE: 4
cccttgaacc tcctcgttcg acc                                         23

<210> SEQ ID NO 5
<211> LENGTH: 23
<212> TYPE: DNA
<213> ORGANISM: Homo sapiens

<400> SEQUENCE: 5
gagacgtgct acttccattt gtc                                         23

<210> SEQ ID NO 6
<211> LENGTH: 356
<212> TYPE: DNA
<213> ORGANISM: Homo sapiens

<400> SEQUENCE: 6
ttttggtgga ctctgctacg tagtggcgtt cagtgaaggg agcagtgttt ttcccagatc    60
ctctggcctc cccgtccccg agggaagcca ggactagggt cgaatgaagg ggtcctccac   120
ctccacgttc cattcctgtt ccacctcaag gtcactggga acacctttcg cagcaaactg   180
ctaattcaat gaagacctgg agggagccaa ttgttccagt tcatctatca catggccagt   240
tggtccattc aacaaatggt tattggatgc ccattatgtg gcaggcactg ttccggggga   300
gagcacacag gtgaactcca gaaagaagaa gctatggccg cagtgattct ggagag       356
```